United States Patent
Yoon et al.

(10) Patent No.: US 11,938,326 B2
(45) Date of Patent: Mar. 26, 2024

(54) METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE

(71) Applicant: Medtronic, Inc., Minneapolis, MN (US)

(72) Inventors: Hyun J. Yoon, Vadnais Heights, MN (US); Wade M. Demmer, Coon Rapids, MN (US); Matthew J. Hoffman, Saint Paul, MN (US); Robert A. Betzold, Fridley, MN (US); Jonathan D. Edmonson, Blaine, MN (US); Michael L. Ellingson, St. Louis Park, MN (US); Mark K. Erickson, Brooklyn Park, MN (US); Ben W. Herberg, Andover, MN (US); Juliana E. Pronovici, New Hope, MN (US); James D. Reinke, Maple Grove, MN (US); Todd J. Sheldon, North Oaks, MN (US); Paul R. Solheim, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 17/675,508

(22) Filed: Feb. 18, 2022

(65) Prior Publication Data

US 2022/0168578 A1 Jun. 2, 2022

Related U.S. Application Data

(62) Division of application No. 16/600,751, filed on Oct. 14, 2019, now Pat. No. 11,253,707, which is a (Continued)

(51) Int. Cl.
*A61N 1/37* (2006.01)
*A61N 1/368* (2006.01)
*A61N 1/39* (2006.01)

(52) U.S. Cl.
CPC .......... *A61N 1/3718* (2013.01); *A61N 1/3684* (2013.01); *A61N 1/3688* (2013.01); *A61N 1/3925* (2013.01); *A61N 1/39622* (2017.08)

(58) Field of Classification Search
CPC .. A61N 1/3718; A61N 1/3684; A61N 1/3688; A61N 1/3925; A61N 1/39622
See application file for complete search history.

(56) References Cited

U.S. PATENT DOCUMENTS 5,174,289 A 12/1992 Cohen
5,978,710 A 11/1999 Prutchi et al.
(Continued)

OTHER PUBLICATIONS

Kloosterman, Dr. E. Martin, MRI Remote Control Study (ROCON). Remote Management of Cardiac Devices Undergoing MRI, received Jan. 26, 2016, 7 pgs.
(Continued)

*Primary Examiner* — Catherine M Voorhees
(74) *Attorney, Agent, or Firm* — WITHERS & KEYS, LLC

(57) ABSTRACT

Implantable medical systems enter an exposure mode of operation, either manually via a down linked programming instruction or by automatic detection by the implantable system of exposure to a magnetic disturbance. A controller then determines the appropriate exposure mode by considering various pieces of information including the device type including whether the device has defibrillation capability, pre-exposure mode of therapy including which chambers have been paced, and pre-exposure cardiac activity that is either intrinsic or paced rates. Additional considerations may include determining whether a sensed rate during the expo-
(Continued)

sure mode is physiologic or artificially produced by the magnetic disturbance. When the sensed rate is physiologic, then the controller uses the sensed rate to trigger pacing and otherwise uses asynchronous pacing at a fixed rate.

20 Claims, 15 Drawing Sheets

Related U.S. Application Data division of application No. 15/487,736, filed on Apr. 14, 2017, now Pat. No. 10,441,798.

(60) Provisional application No. 62/323,574, filed on Apr. 15, 2016.

(56) References Cited

U.S. PATENT DOCUMENTS

| | | | |
|---|---|---|---|
| 6,937,906 B2 | 8/2005 | Terry et al. | |
| 7,050,855 B2 | 5/2006 | Zeijlemaker et al. | |
| 7,076,283 B2 | 7/2006 | Cho et al. | |
| 7,697,988 B2 * | 4/2010 | Clement | A61N 1/37 607/17 |
| 8,014,867 B2 | 9/2011 | Cooke et al. | |
| 8,046,063 B2 | 10/2011 | Betzold | |
| 8,433,408 B2 | 4/2013 | Ellingson et al. | |
| 8,467,882 B2 | 6/2013 | Ellingson et al. | |
| 8,554,318 B2 | 10/2013 | Legay | |
| 8,737,862 B2 | 5/2014 | Manico et al. | |
| 8,744,578 B2 | 6/2014 | Ellingson | |
| 8,805,496 B2 | 8/2014 | Ellingson | |
| 8,818,506 B2 | 8/2014 | Legay | |
| 8,886,317 B2 | 11/2014 | Cooke et al. | |
| 9,095,721 B2 | 8/2015 | Stancer et al. | |
| 9,138,584 B2 | 9/2015 | Stancer et al. | |
| 9,174,058 B2 | 11/2015 | Ellingson et al. | |
| 2003/0144705 A1 * | 7/2003 | Funke | A61N 1/37 607/27 |
| 2003/0144706 A1 * | 7/2003 | Funke | A61N 1/37 607/30 |
| 2004/0024421 A1 | 2/2004 | Ideker et al. | |
| 2006/0167496 A1 | 7/2006 | Nelson et al. | |
| 2010/0137945 A1 | 6/2010 | Gadagkar et al. | |
| 2011/0077706 A1 * | 3/2011 | Ellingson | A61N 1/3718 607/59 |
| 2011/0160791 A1 | 6/2011 | Ellingson et al. | |
| 2011/0196450 A1 * | 8/2011 | McClure | A61N 1/37 607/60 |
| 2012/0221068 A1 | 8/2012 | Ellingson | |
| 2013/0289384 A1 | 10/2013 | Jenison et al. | |
| 2014/0100624 A1 | 4/2014 | Ellingson | |
| 2016/0151623 A1 | 6/2016 | Doerr | |
| 2016/0151624 A1 | 6/2016 | Doerr | |
| 2017/0296827 A1 | 10/2017 | Yoon et al. | |
| 2017/0296835 A1 | 10/2017 | Yoon et al. | |

OTHER PUBLICATIONS

Kloosterman, Dr. E. Martin, MRI Remote Control Study (ROCON). Remote Management of Cardiac Devices Undergoing MRI, received Mar. 3, 2016, 30 pgs.

Kloosterman, Dr. E. M., "Novel MRI Safe Mode Selection Algorithm Standardized Real-Time Solution for a Variable Time-Dependent Problem", J. Clin Exp. Cardiology, Dec. 11-12, 2017, 22nd World Cardiology Conference.

\* cited by examiner

METHODS AND IMPLANTABLE MEDICAL SYSTEMS THAT IMPLEMENT EXPOSURE MODES OF THERAPY THAT ALLOW FOR CONTINUED OPERATION DURING EXPOSURE TO A MAGNETIC DISTURBANCE

CROSS REFERENCE TO RELATED APPLICATIONS

This application is a division of U.S. patent application Ser. No. 16/600,751, filed Oct. 14, 2019 (published as U.S. Patent Publication No. US 2020/0038665), which is a division of U.S. patent application Ser. No. 15/487,736, filed Apr. 14, 2017 (published as U.S. Patent Publication No. 2017/0296835), which claims the benefit of the filing date of provisional U.S. Patent Application No. 62/323,574, filed Apr. 15, 2016, the content of all of which are incorporated by reference in their entirety.

TECHNICAL FIELD

Embodiments relate to implantable medical devices that provide modes of therapy such as providing cardiac pacing. More specifically, embodiments relate to implantable medical systems that allow for an exposure mode of therapy to be controlled to allow for continued operation during exposure to a magnetic disturbance like that created by a magnetic resonance imaging (MM) scan or other medical procedures.

BACKGROUND

Implantable medical devices may perform various functions in order to deliver modes of therapy to a patient. For example, cardiac stimulation devices like pacemakers and defibrillators may sense electrical physiologic signals in some modes of therapy in addition to providing electrical pacing signals to one or more chambers of the heart. Some modes of therapy that sense a physiologic signal then use that signal when determining how to control the pacing signal.

Patients that have an implantable medical device may be exposed to magnetic disturbances like those caused by MM scans or other medical procedures. These magnetic disturbances may result in the device sensing signals that are not actually physiologic but are artificially created by the magnetic disturbances. If the device is allowed to control the pacing signal based on the sensed artificial signal, then the pacing signal may be inappropriate or even harmful for the patient. Therefore, it is commonplace to utilize an exposure mode of therapy during such disturbances where the exposure mode deactivates sensing or otherwise ignores the sensed signal and paces asynchronously in a pre-defined pacing configuration with a pre-defined pacing rate. This may not be an optimal exposure mode of therapy, especially for certain patients having particular device types such as those with pacing ability but being primarily for defibrillation purposes. Likewise, the pre-defined pacing rate may not be an optimal rate of pacing for patients with other pacing needs.

SUMMARY

Embodiments address issues such as these and others by applying various considerations in order to determine an appropriate mode of therapy and/or an appropriate rate when the device is in an exposure mode such as during times when a magnetic disturbance is present. For instance, the type of device may be considered to determine whether a pace capable device is primarily for pacing only or for defibrillation or for cardiac resynchronization with defibrillation abilities. A measure of the prior rate of cardiac activity, such as an average of a prior intrinsic rate or of a prior pacing rate, may be factored into the determination of an appropriate asynchronous rate. Additionally, the device may continue to sense the intrinsic rate and then analyze that intrinsic rate to determine whether the intrinsic rate is physiologic or artificial. The pacing mode may then be set to use a physiologic intrinsic rate to trigger the pacing signal or to use the asynchronous pacing rate and ignore an artificial intrinsic rate.

Embodiments provide methods and devices controlling an exposure mode of therapy of an implantable medical device. A device type of the implantable medical device is determined and upon detecting a need to switch to the exposure mode, the exposure mode of therapy of the implantable medical device is selected based on the device type and a pre-exposure mode of therapy. The exposure mode of therapy is implemented at the implantable medical device by performing a first sensing of a heart rate and when the first sensing of heart rate indicates at least a first amount of noise is present, implementing an asynchronous pacing mode and then making adjustments to at least one sensing setting prior to a next sensing of the heart rate and when the first sensing of heart rate indicates that at least the first amount of noise is not present, then implementing a triggered pacing mode.

Embodiments provide methods and devices controlling an exposure mode of therapy of an implantable medical device. A type of an implantable medical device is determined by determining whether the implantable medical device is capable of providing a therapy to multiple chambers of a heart. When the implantable medical device is not a type capable of providing therapy to multiple chambers of the heart, then it is determined if the device is of a type capable of defibrillation therapy. When the device is not capable of defibrillation therapy then a pacing percentage of the device is compared to a first threshold. When the device is capable of defibrillation therapy then the pacing percentage of the device to a second threshold. The exposure mode is selected based on device type and the pre-exposure mode by implementing a pacing mode that paces a same chamber of the heart as the pre-exposure mode when the pacing percentage exceeds the first threshold when the device is not capable of defibrillation therapy or the second threshold when the device is capable of defibrillation therapy.

Embodiments provide methods and devices for controlling an exposure mode of therapy of an implantable medical device by determining if the device is a defibrillator type and if so, then determining if a lower pacing rate is lower than a rate threshold and if a ventricular pacing percentage is lower than a pacing percentage threshold. If the lower pacing rate is lower than the rate threshold and the pacing percentage is lower than the pacing percentage threshold, then choosing a non-pacing mode as the exposure mode of therapy. If the lower rate is not lower than the rate threshold and/or the pacing percentage is not lower than the pacing percentage, then choosing a permanent pacing mode as the exposure mode of therapy.

Embodiments provide methods and devices for controlling an exposure mode of therapy of an implantable medical device by determining if a heart rate exceeds a first threshold. If not, then a pacing rate for the exposure mode is set to the heart rate plus a first adjustment. If so, then it is determined if the heart rate exceeds a second threshold that is higher than the first and if a ventricular pacing percentage exceeds a pacing percentage threshold. If the heart rate does not exceed the second threshold and/or the ventricular pacing percentage does not exceed the pacing percentage threshold, then a pacing rate for the exposure mode is set to the heart rate plus a second adjustment but limited to a specified maximum. If the heart rate does exceed the second threshold, the ventricular pacing percentage does exceed the pacing percentage threshold, and the device type is other than a resynchronization therapy device, then the pacing rate is set to a fixed amount that is higher than the first threshold and lower than the second threshold and a pacing mode is set to VOO. If the heart rate does exceed the second threshold, the ventricular pacing percentage does exceed the pacing percentage threshold, and the device type is a resynchronization therapy device, then the pacing rate is set to the heart rate plus the second adjustment but limited to the specified maximum.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Embodiments provide an implantable medical system that employs various considerations to determine an appropriate exposure mode of therapy such as during times when the system is exposed to a magnetic disturbance. Considerations may include the type of implantable medical device that is present in the system and the manner of use of the device in pre-exposure modes. Considerations may also include whether a sensed intrinsic signal is physiologic and therefore reliable for triggering pacing or artificial and therefore unreliable. Considerations may further include pre-exposure mode rates.

Figure 1:
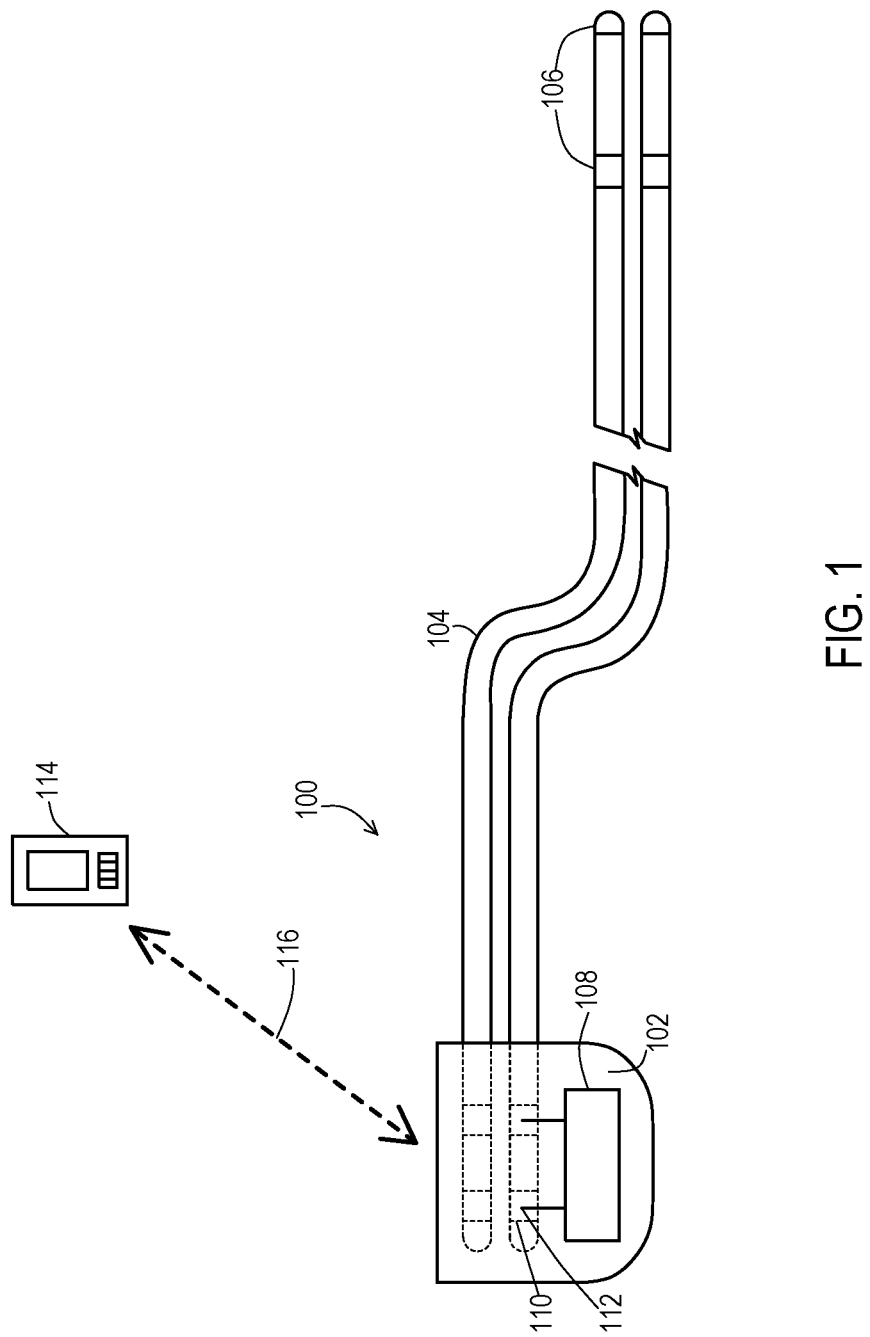
FIG. 1 shows an example of an implantable medical system that may operate according to various embodiments disclosed herein.

FIG. 1 shows an example of an implantable medical system according to embodiments disclosed herein. A patient receives an implantable medical system 100 which, in this example, implantable medical system 100 includes an implantable medical device 102 that has the ability to perform electrical sensing and pacing. The implantable medical device (IMD) 102 may be of various types and some of those types may offer additional functionality such as defibrillation and/or cardiac resynchronization therapy. The IMD 102 may even be primarily for non-pacing functions like defibrillation and/or cardiac resynchronization although may include the ability to pace if needed. A collection 108 of electrical components is included to provide these functions.

The implantable medical system 100 in some cases may also include one or more electrical leads 104. The electrical lead(s) 104 are electrically connected to the IMD 102 via proximal contacts 110 on the leads 104 and electrical connectors 112 of the IMD 102. The leads 104 include electrodes 106 on a distal end that interface with the body tissue to capture electrical physiologic signals or deliver electrical pacing signals.

The implantable medical system 100 in some cases may omit the use of electrical leads 104. In this embodiment, electrodes 106 integrated into the IMD 102 that interface with the body tissue to capture electrical physiologic signals or deliver electrical pacing signals.

Additionally, in some cases the implantable medical system 100 may include external devices 114 such as hand-held controllers that are capable of communicating wirelessly with the IMD 102. The wireless communications 116 may be near field, arm's length, far field and the like as is known in the art. The external device 114 may generate commands to the IMD 102 to request information about the IMD 102 and/or to instruct the IMD 102 to operate in a particular way. In particular, in some cases the external device 114 may be used to manually switch the IMD 102 to enter an exposure mode of therapy. Alternatively or additionally, the IMD 102 may have the ability to automatically detect magnetic disturbances and then automatically enter an exposure mode of therapy.

Figure 2:
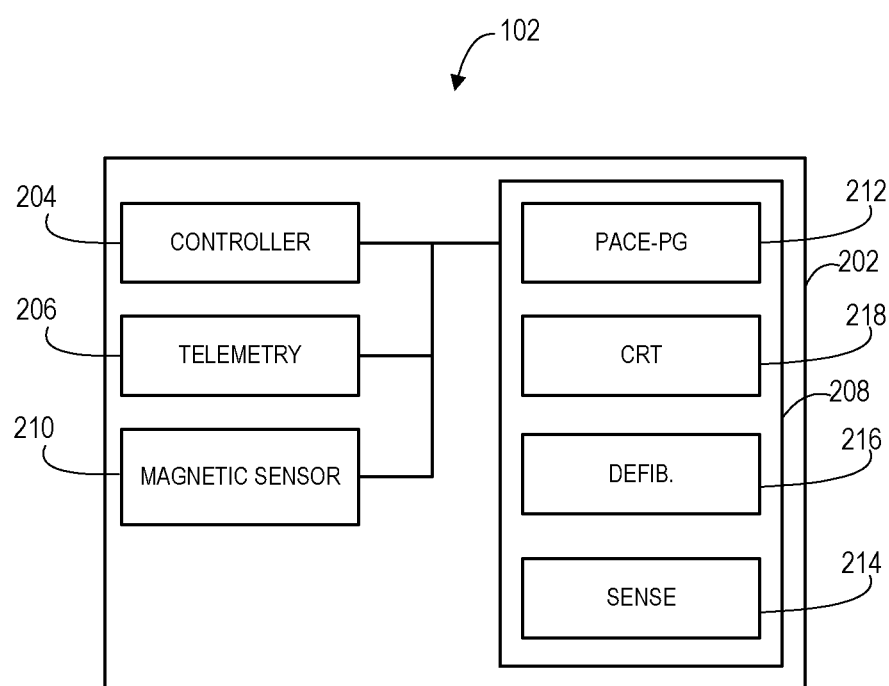
FIG. 2 shows an example of components of the implantable medical system.

FIG. 2 shows an example of components of an IMD 102. The IMD 102 may include a housing 202 that contains the various components. The IMD 102 includes a controller 204 that may control the operations of the IMD 102 by communicating with other components. The controller 204 may be of various forms such as a general purpose programmable processor, a dedicated purpose processor, hardwired digital logic, and the like. The controller may also include internal or external memory having computer-readable instructions that, when executed by controller 204 cause controller 204 to perform various operations attributed to it in this disclosure. The memory may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The IMD 102 may include telemetry 206 to communicate wireless with external devices such as the external device 114. As discussed above, the IMD 102 may communicate via one or more types of wireless communications including near field, arm's length, far field and the like. For instance, the telemetry 206 may include inductive coupling for near field or arm's length, may include radio frequency far field functions such as those operating in the Medical Implant Communication Service (MICS) band.

The IMD 102 also includes a therapy device 208 that may include one or more engines for providing various therapy functions. For instance, the therapy device 208 may include a configurable pacing engine 212 that may pace one or more chambers of the heart via corresponding one or more electrodes of the lead 106. The therapy device 208 may include a configurable sensing engine 214 to sense from one or more chambers of the heart. Likewise, depending upon the type of IMD 102, the therapy device 208 may include a defibrillation engine 216 capable of providing high voltage defibrillation shocks. Again depending upon the type of IMD 102, the therapy device 208 may include a cardiac resynchronization engine 218 capable of providing cardiac resynchronization signals. In some embodiments a single "engine" may be used for multiple types of therapy, such as a single pacing engine that provides bradycardia pacing, anti-tachycardia pacing and/or cardiac resynchronization pacing therapy.

The engine(s) may be implanted in the form of one or more modules. For instance, a therapy delivery module may provide the pacing, resynchronization, or/or defibrillation functions. In one example, an engine may include a low voltage (LV) therapy module for delivering low voltage pacing pulses using an extra-cardiovascular pacing electrode vector selected from various electrodes. LV therapy module may be configured to deliver low voltage pacing pulses, e.g., 8 V or less or 10 V or less. One or more capacitors included in the LV therapy module are charged to a voltage according to a programmed pacing pulse amplitude by a LV charging circuit, which may include a state machine. The LV charging circuit may charge the capacitors to a multiple of the voltage of a battery included in a power source without requiring a transformer. At an appropriate time, the LV therapy module couples the capacitor(s) to a pacing electrode vector to deliver a pacing pulse to the heart.

An engine may additionally or alternatively include a high voltage (HV) therapy module that includes one or more high voltage capacitors. When a shockable rhythm is detected, the HV capacitor(s) is(are) charged to a shock voltage amplitude by a HV charging circuit according to the programmed shock energy. The HV charging circuit may include a transformer and be a processor-controlled charging circuit that is controlled by a control module. The control module applies a signal to trigger discharge of the HV capacitor(s) upon detecting a feedback signal from therapy delivery module that the HV capacitors have reached the shock voltage amplitude required to deliver the programmed shock energy. In this way, control module controls operation of the high voltage therapy module to deliver CV/DF shocks using defibrillation electrodes and/or a device housing.

HV therapy module may be used to deliver cardiac pacing pulses. In this case, the HV capacitor(s) is(are) charged to a much lower voltage than that used for delivering shock therapies but may be higher than the maximum available pulse voltage amplitude produced by the LV therapy module. For example, the HV capacitor may be charged to 40 V or less, 30 V or less, or 20 V or less for producing extra-cardiovascular pacing pulses.

Compared to pacing pulses delivered by LV therapy module, pulses delivered by HV therapy module may have a higher voltage amplitude and relatively longer pulse width for delivering higher energy pacing pulses for capturing the heart. More current may be delivered using a low impedance pacing electrode vector. Longer pulse width is attainable due to a higher capacitance (and consequently higher RC time constant) of the HV capacitor(s). The LV therapy module may be capable of producing a maximum pulse voltage amplitude of up to and including 10 V. The maximum single-pulse pacing pulse width produced by LV therapy module may be 2 ms. In some examples, LV therapy module may be configured to produce composite pacing pulses comprising two or more individual pulses fused in time to deliver a cumulative composite pacing pulse energy that captures the heart. Techniques for delivering composite pacing pulses are generally disclosed in the U.S. patent application Ser. No. 15/367,516 and in provisional U.S. Pat. Application No. 62/262,412 and corresponding pending U.S. patent application Ser. No. 15/368,197, all of which are incorporated herein by reference in their entirety. The maximum composite pacing pulse width may be up to 8 ms or higher.

Additionally, the IMD 102 may include one or more sensors 210 for detecting magnetic disturbances. For instance, Hall effect sensors may be used to detect that a magnetic field of a particular intensity is present. This allows the controller 204 to then enter an exposure mode. The controller 204 may then distinguish whether the magnetic field is representative of a programming trigger caused by a programming magnet being placed near the site of implantation of the IMD 102 or is a magnetic disturbance like that from an MRI machine or other source that necessitates an exposure mode of therapy. For instance, the controller 204 may utilize various techniques to distinguish the programming magnet from an MRI machine. Examples include determining magnetic field strength particularly at multiple locations, determining force resulting from the magnetic field, determining torque resulting from the magnetic field, determining magnetic field direction particularly as measured at multiple locations, and the like to then determine if threshold are met that are indicative of a magnetic field from an MRI machine. Examples of such techniques are disclosed in U.S. application Ser. Nos. 13/046,158; 13/456,891; 13/587,368; and Ser. No. 14/340,893, all of which are incorporated by reference herein in their entirety.

Figure 3:
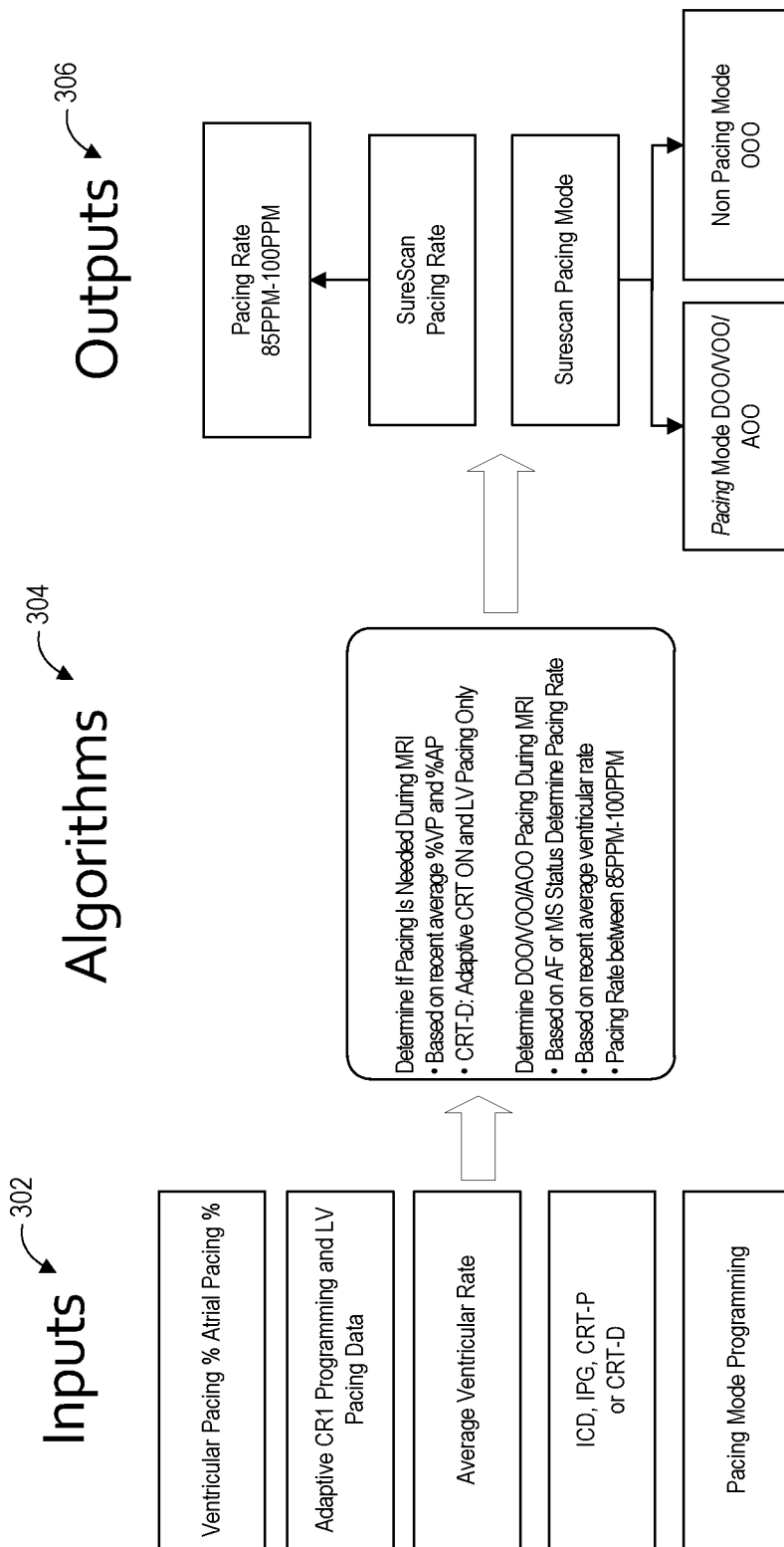
FIG. 3 shows an example of inputs, considerations, and resulting output decisions when implementing an exposure mode of operation at the implantable medical system.

FIG. 3 shows a basic flow of information that may be used by a controller, such as a controller within the external device 114 or the internal controller 204 of the IMD 102, to make a determination as to the appropriate exposure mode and rate of therapy that should be employed. This basic flow of information may be used to invoke the appropriate exposure mode once it has been detected, either by manual programming or by automatic detection, that the IMD 102 should switch to the exposure mode. The controller may gather information to be used as inputs 302. Examples of the inputs include various pieces of information from the pre-exposure mode operation such as: pacing percentage for both ventricular and atrial pacing; adaptive and/or general cardiac resynchronization therapy programming including which ventricles are being stimulated; the average atrial and/or ventricular rate of pacing; the type of device including whether the device is an implantable cardiac defibrillator (ICD), an implantable pulse generator (IPG) primarily for pacing, a cardiac resynchronization therapy (CRT) device with pacing ability but not defibrillation, or a CRT device that also includes defibrillation ability; and pacing mode programming including which chambers are being paced.

The controller may then process this input information 302 via considerations 304. For instance, the controller may determine whether pacing is even needed during the period of time that exposure mode is active, such as during an MRI scan. Factors include what the prior pacing percentage is and in the case of CRT, whether the cardiac resynchronization stimulation is only being applied to the left ventricle or to other chambers.

The considerations 304 may also include determining what the pacing mode should be if pacing is needed, such as whether to pace the atrium, ventricle, or both. This may be based on the pre-exposure programming as well as current status such as whether atrial fibrillation is occurring and whether a mode switch due to atrial fibrillation is warranted to avoid wasting atrial pacing signals.

The considerations 304 may also include determining the pacing rate. For using asynchronous mode of pacing, the fixed rate may be based on a pre-exposure mode factor such as the average ventricular rate. Furthermore, consideration may be given to a pre-defined range of rates. For instance, for a given patient, it may be desirable to contain the fixed rate to somewhere between 85 and 100 paces per minute. As discussed below in reference to FIG. 5A, in some embodiments it may be desirable to also consider whether it is possible to sense an intrinsic rate that is physiologic rather than artificial while in the exposure mode and in that case trigger pacing from the intrinsic rate rather than using asynchronous pacing at the previously established asynchronous rate. The result of these considerations 304 is to produce outputs 306 necessary to implement the particular exposure pacing mode rate.

Figure 4:
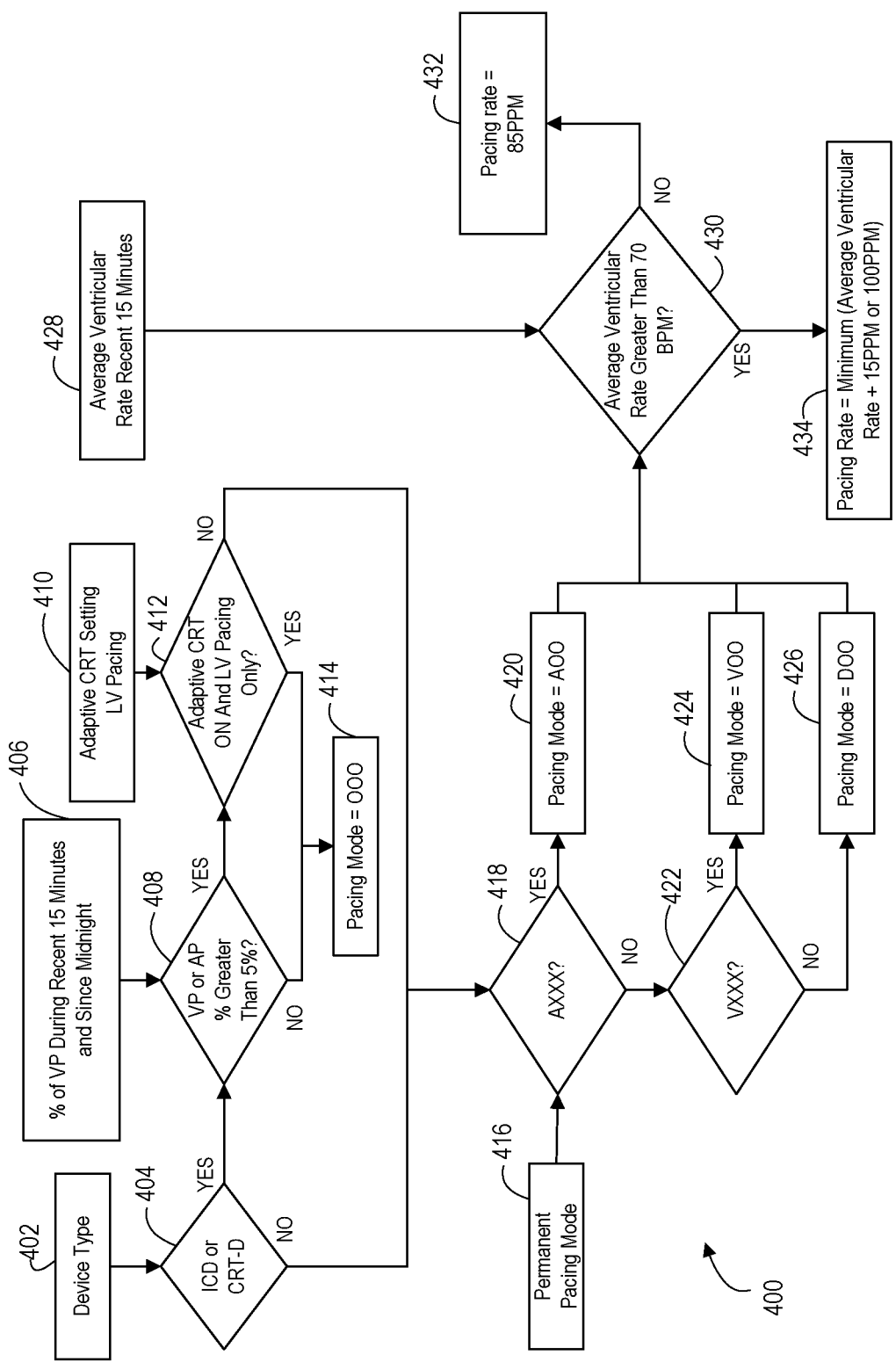
FIG. 4 shows an example of logical operations that may be performed by the implantable medical system to consider device type and prior rate of cardiac activity when establishing the exposure mode of therapy.

FIG. 4 shows an example 400 of logical operations that a controller may employ to ultimately select the pacing mode and rate for the exposure mode of therapy. Initially, the type of IMD 102 is determined at a query 404 that accesses the device type information 402. For instance, where the controller performing these operations is the external device 114 being used to manually program the IMD 102 to enter the exposure mode, the external device 114 may send a wireless request for information at the query 404 to obtain the device type 402 from the IMD 102. Where the controller 202 of the IMD 102 is the controller performing these operations either in response to a command from the external device 114 to enter the exposure mode or where the IMD 102 has detected the magnetic disturbance and has automatically entered the exposure mode, then the controller 202 accesses the locally stored device type information 402.

Regardless of which device performs these operations, query operation 404 determines from the device type information 402 whether the IMD 102, and specifically the therapy device 208, is of the type that can provide defibrillation. For instance, query operation 404 may specifically check for an ICD or a CRT device with defibrillation. Operational flow then proceeds to a query operation 408 when the IMD 102 does have defibrillation ability or proceeds to query operation 418 when the IMD 102 does not have defibrillation ability.

It is also to be appreciated that an external device 114 may implement the query 404 and then provide the IMD 102 with instruction regarding whether the controller 204 should then proceed with the remainder of these operations by beginning at the query operation 408 or at the query operation 418. The controller 204 may then proceed with the remainder of these operations where the controller 204 then utilizes pre-exposure mode information without being required to uplink that information to the external device 114. However, where the external device 114 performs all of these operations or where the query 404 is based to some degree on pre-exposure mode programming (e.g., CRT-D with defibrillation deactivated to behave as a CRT-P), then the pre-exposure mode information is uplinked from the IMD 102 to the external device 114 and the external device 114 downlinks the instruction for the proper exposure mode and rate.

It is also to be noted that at query operation 404, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 4 that stems from the query operation 404. In that case, the initial programming being loaded onto the IMD 102 from the manufacturer utilizes the device type information 402 to specify in the initial programming which query operation should be the first operation to be performed by the IMD 102 upon automatically entering exposure mode, either query operation 408 or query operation 418. In that case, the IMD 102 need not perform the query operation 404 upon entering the exposure mode since that query 404 was already resolved at the time of initial programming.

In any of these alternatives above, operational flow proceeds to query 408 where the device type is such that defibrillation is available and proceeds to the query operation 418 otherwise. For device types leading to the query operation 408, the controller determines from pacing percentage information 406 stored by the IMD 102 whether the pacing percentage (considering either atrial or ventricular) is greater than a threshold. The pacing percentage information 406 may be based on pacing activity for some pre-exposure period immediately preceding the exposure mode, such as 15 minutes or for the entire day such as since midnight. For example, query 408 may determine whether the IMD 102 has been pacing the ventricle more than 5% of the pacing cycles for the 15 minutes preceding the exposure mode. It will be appreciated that other pacing percentage thresholds may also be applied but 5% is believed to be effective for most patients. If the pacing percentage is lower than the threshold, this indicates that it is appropriate for the patient to go without pacing for a short time such as for the duration of an MM scan, and in that case the controller selects that there be no pacing via pacing mode OXO for the exposure mode as indicated at pacing state 414. While pacing state 414 shows the pacing mode as OOO, it will be appreciated that this is just one example of the OXO modes that may be used.

If the pacing percentage is at the query operation 408 is greater than the pacing threshold, then the controller determines at a query operation 412 whether the device is performing adaptive and/or general CRT with left ventricle pacing only by referencing the pre-exposure mode information 410. If CRT is being used with only left ventricle pacing, then even though the pacing percentage is above the threshold, it is still appropriate to stop the left ventricle pacing for a short period of time and the controller selects that there be no pacing for the exposure mode as pacing mode OXO as indicated at pacing state 414.

If the controller finds that CRT is being used and more than merely left ventricle pacing is occurring, then the controller concludes that some form of pacing is needed. Therefore, the controller then proceeds to the query operation 418 just as if query operation 404 had not found that the device was defibrillation capable (i.e., that the IMD 102 is a type that is primarily for pacing instead of primarily for defibrillation).

At the sequence of query operations 418 and 422, the controller then determines what the pre-exposure pacing mode has been by referencing the pre-exposure mode pacing mode information 416. This pre-exposure pacing mode, also referred to as the permanent pacing mode, is AXX/AXXR, VXX/VXXR, or DXX/DXXR. The controller sets the exposure mode to pace the same set of chambers as the pre-exposure mode, so where the pre-exposure pacing mode is AXX/AXXR, then in this embodiment the controller selects that there be atrial pacing for the exposure mode by using asynchronous pacing mode AOO as indicated at pacing state 420. Where the pre-exposure pacing mode is VXX/VXXR, then in this embodiment the controller selects that there be ventricular pacing for the exposure mode by using asynchronous pacing mode VOO as indicated at pacing state 424. Where the pre-exposure pacing mode is DXX/DXXR, then in this embodiment the controller selects that there be dual chamber pacing for the exposure mode by using asynchronous pacing mode DOO as indicated at pacing state 426.

Once the pacing mode for the exposure mode has been set, the controller then proceeds to a query operation 430 to determine an appropriate exposure mode pacing rate for the chosen pacing mode. The query operation 430 determines whether a pre-exposure mode rate of cardiac activity as specified in pre-exposure mode information 428 exceeds a rate threshold. The pre-exposure mode information 428 may be one of various different pieces of information. For example, the pre-exposure mode information 428 may specify an average ventricular rate taken over a 15 minute period immediately preceding the exposure mode. This pre-exposure mode average rate may be an average intrinsic rate that has been sensed or it may be an average paced rate.

It will be appreciated that the rate threshold applied at the query operation 430 may vary but it has been found that 70 beats per minute is an effective example. If the threshold is not exceeded by the pre-exposure mode pacing rate, then the controller sets the asynchronous pacing rate to a pre-defined fixed value such as 85 beats per minute as indicated at the pacing rate state 432. It will be appreciated that this pre-defined fixed value may vary, but 85 beats per minute are known to be acceptable for most patients. If the threshold is exceeded by the pre-exposure mode rate, then the controller sets the asynchronous pacing rate to a fixed value that is equal to the pre-exposure mode rate plus a fixed adjustment but with an upper limit at the pacing rate state 434. For example, the controller may set that asynchronous pacing rate to the pre-exposure rate plus 15 additional paces per minute with an upper limit of 100 paces per minute. The fixed adjustment may vary but it has been found that an adjustment of 15 additional paces per minute adequately avoids a competitive pacing condition. Furthermore, the upper limit may vary but it has been found that an upper limit of 100 paces per minute is adequate. Therefore, in this particular example, the pacing rate for the exposure mode will be set within the range of 85-100 paces per minute.

Figure 5A:
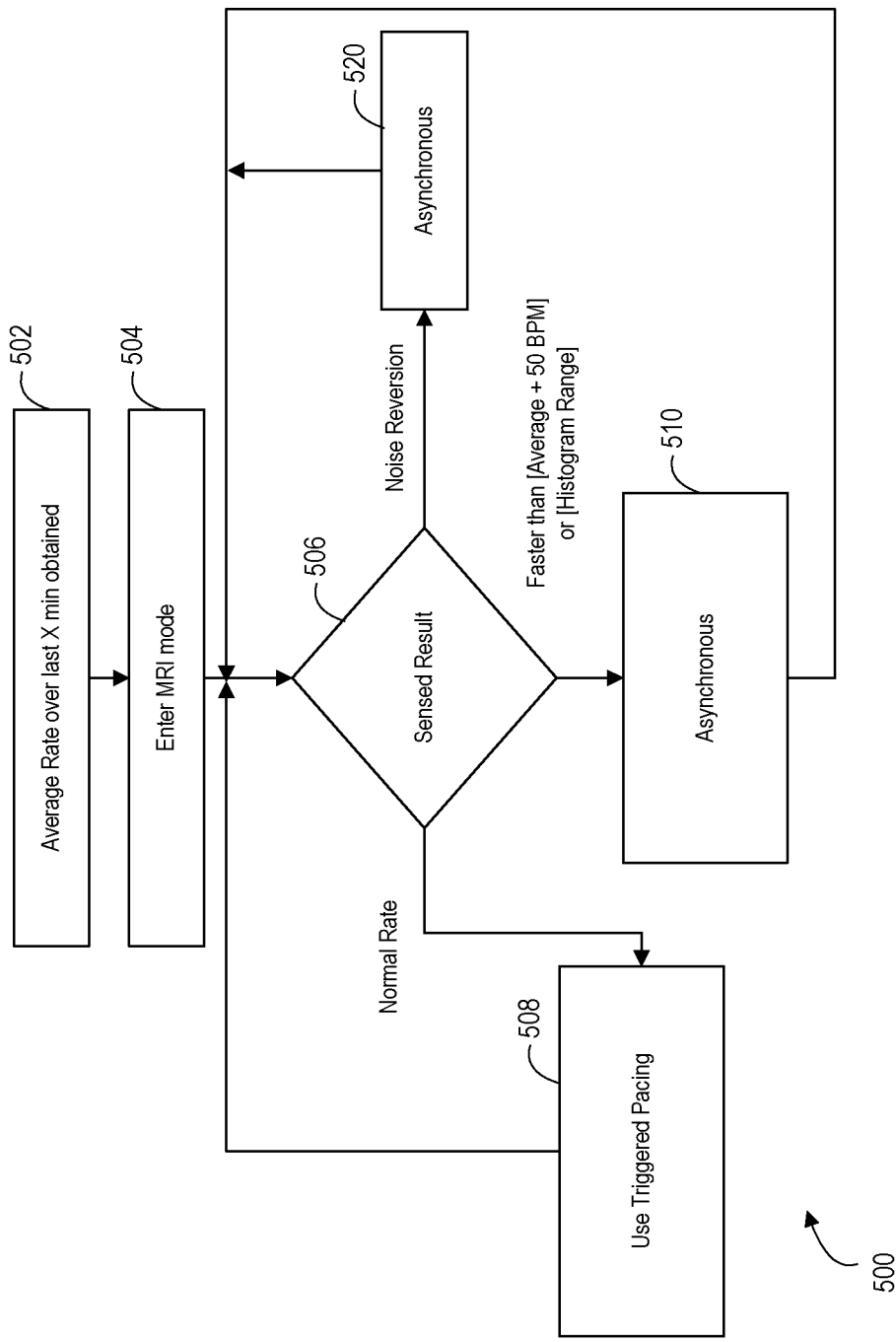
FIG. 5A shows a first example of logical operations that may be performed by the implantable medical system to consider whether a sensed intrinsic rate is physiologic or artificial and whether to utilize triggered pacing or asynchronous pacing as the exposure mode of therapy.

FIG. 5A shows an example 500 of logical operations that may be used by the controller 204 to continuously adapt the exposure mode to use a triggered pacing mode when possible and to otherwise use an asynchronous fixed pacing rate. In this example, the average rate, either intrinsic or paced, over some period of time preceding the exposure mode is obtained at the rate operation 502. When needed, the exposure mode, also referred to as the Mill mode, is entered at the operation 504. The controller then begins monitoring the sensing for an intrinsic rate at a query operation 506.

Because a magnetic disturbance may result in sensing an artificial intrinsic rate that is not appropriate for triggering pacing, the controller 204 utilizes logic at the query operation 506 to determine whether the sensed rate is a normal rate, a faster than normal rate, or a noise reversion which occurs where the rate may be within the normal range but an abrupt change within the range is artificial. The controller compares the sensed rate to at least one reference value, as discussed in more detail below, to make the determination.

When the sensed rate is determined to be normal by the controller, then the controller sets the exposure mode to triggered pacing of the chambers that were being paced in the pre-exposure mode as indicated at the triggered pacing state 508. Thus, the triggered pacing mode may be AAT, VVT, or DDT. The normal rate may be confirmed by using a range of rates known to be normal in general as the reference values to compare against the sensed rate. Alternatively, the reference values to compare to the sensed rate may be more specific to this particular patient by establishing an upper limit for the range of normal rates by utilizing the average intrinsic or paced pre-exposure rate plus an adjustment. As another alternative, the normal rate may be established by maintaining a statistical distribution, such as a histogram, of historical pacing/sensing data and choosing the normal range to be those within a particular range of percentiles. Such a histogram or other statistical distribution may instead be used to determine the adjustment to the average pre-exposure rate by choosing a rate in a larger percentile as the upper limit of the normal range. For example, the upper limit to the normal rate may be the average pre-exposure rate plus 50 beats per minute.

Where the controller detects that the sensed rate falls outside of the normal range, then the controller sets the exposure mode to asynchronous fixed rate pacing as indicated at the pacing state 510. This ensures that the sensed rate, which is possibly artificial, does not produce an inappropriate pacing rate.

Where the controller detects that the sensed rate indicates a noise reversion, then the controller sets the exposure mode to asynchronous fixed rate pacing as indicated at the pacing state 520. The controller may detect the noise reversion by comparing a current sensed rate to immediately prior sensed rates collected during a set period of time that precedes the sensing of the current intrinsic rate and looking for abrupt changes to the sensed rate that are artificial rather than physiologic. This may be done by comparing a difference in the current and prior sensed rates to a threshold where the threshold is chosen to distinguish a physiologic change in rate from an artificial one. For example, a near instantaneous change of 50 beats per minute is more likely to be artificial than physiologic.

Thus, using this example of FIG. 5A, the IMD 102 may enter an exposure mode and may transition as needed from triggered pacing to asynchronous pacing. It will be appreciated that the example of FIG. 5A may be used in conjunction with the example of FIG. 4 to also control the exposure mode based on device type. For instance, if the IMD 102 is primarily for defibrillation or CRT with defibrillation and the pacing percentage is low, then pacing may be avoided altogether, but when the example of FIG. 4 determines that pacing should be done while in exposure mode, then the example of FIG. 5A may be further employed to transition between triggered pacing and asynchronous pacing based on the results of analyzing the sensed rate.

Figure 5B:
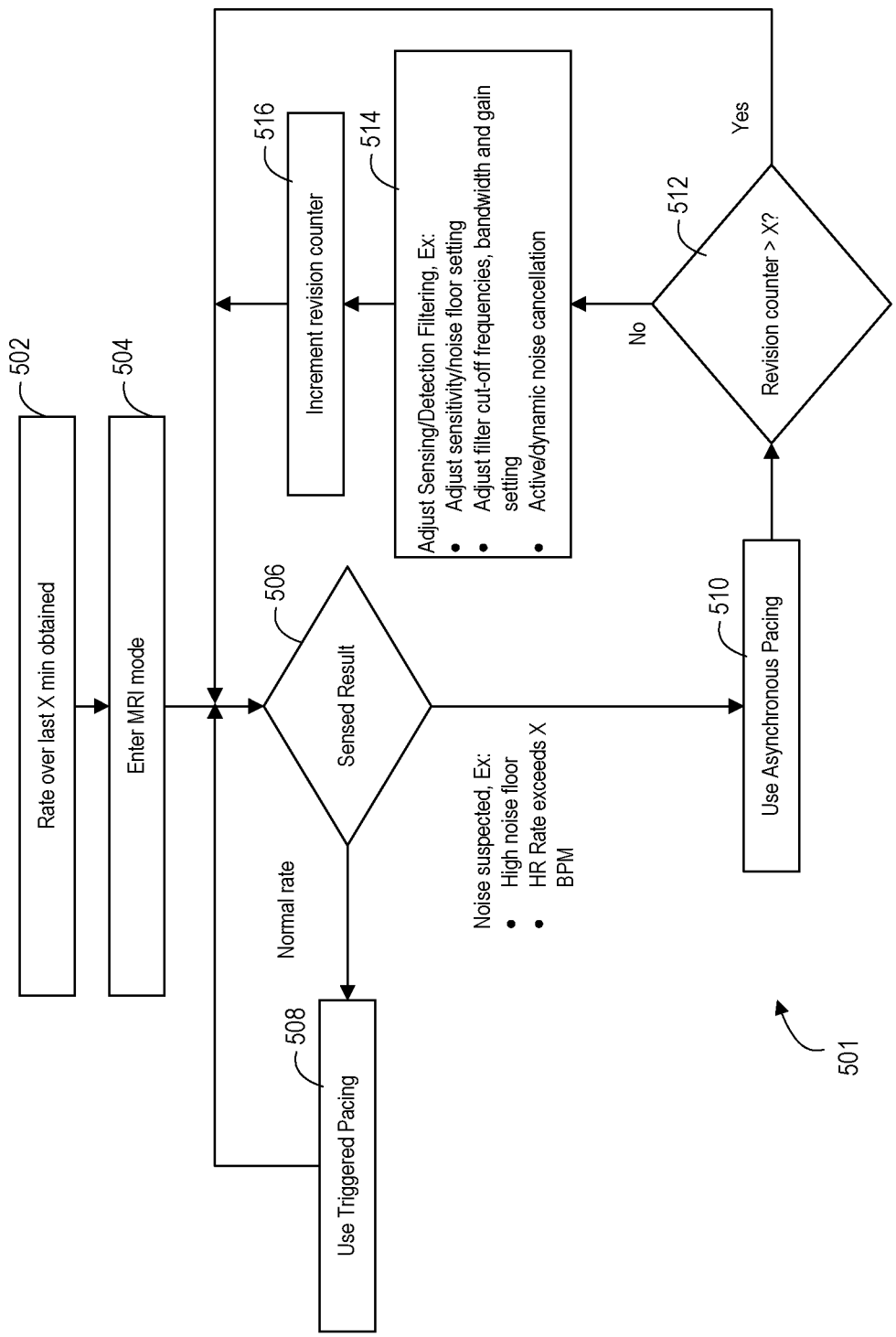
FIG. 5B shows a second example of logical operations that may be performed by the implantable medical system to consider whether a sensed intrinsic rate is physiologic or artificial and whether to utilize triggered pacing or asynchronous pacing as the exposure mode of therapy.

FIG. 5B shows a second example 501 of logical operations that is similar to FIG. 5A with the operations 502, 504, 506, 508, and 510 being the same as described above for FIG. 5A. However, when the query operation 506 detects that the sensed intrinsic rate is higher than the normal physiologic range and/or senses a high noise floor, asynchronous mode is chosen at asynchronous state 510 which leads to a query operation 512. Here, it is detected whether a revision counter that is incremented as discussed below now exceeds a revision counter threshold. This threshold may be set to various amounts depending upon preference for how many attempts are desired to try to enter or re-enter triggered pacing mode upon noise being found. If the threshold is exceeded, then operational flow returns to the query operation 506 to continue sensing with the current sensing parameters. If the threshold is not exceeded, then operational flow proceeds to an operation 514.

At the operation 514, the sensing parameters may be adjusted so that the sensed signal may be reconsidered using the adjusted parameters in order to potentially eliminate the noise. Eliminating the noise allows the physiologic portion of the sensed signal to be revealed and if within the physiologic range then used to successfully perform triggered pacing via the triggered pacing state 508. Examples of adjusting the sensing parameters include adjusting the sensitivity of the sensing in terms of changing the noise floor threshold. Another example includes adjusting filter cut-off frequencies, bandwidth, and gain settings. Another example includes applying active or dynamic noise cancellation. Once the adjustment is made, the revision counter may be incremented at an operation 516 and then operational flow proceeds to the query operation 506 to continue sensing using the new sensing parameters. If the sensed result is within the normal physiologic range, then the triggered pacing mode is used via the triggered pacing state 508. Otherwise, asynchronous pacing mode continues via the asynchronous pacing state 510.

Figure 6:
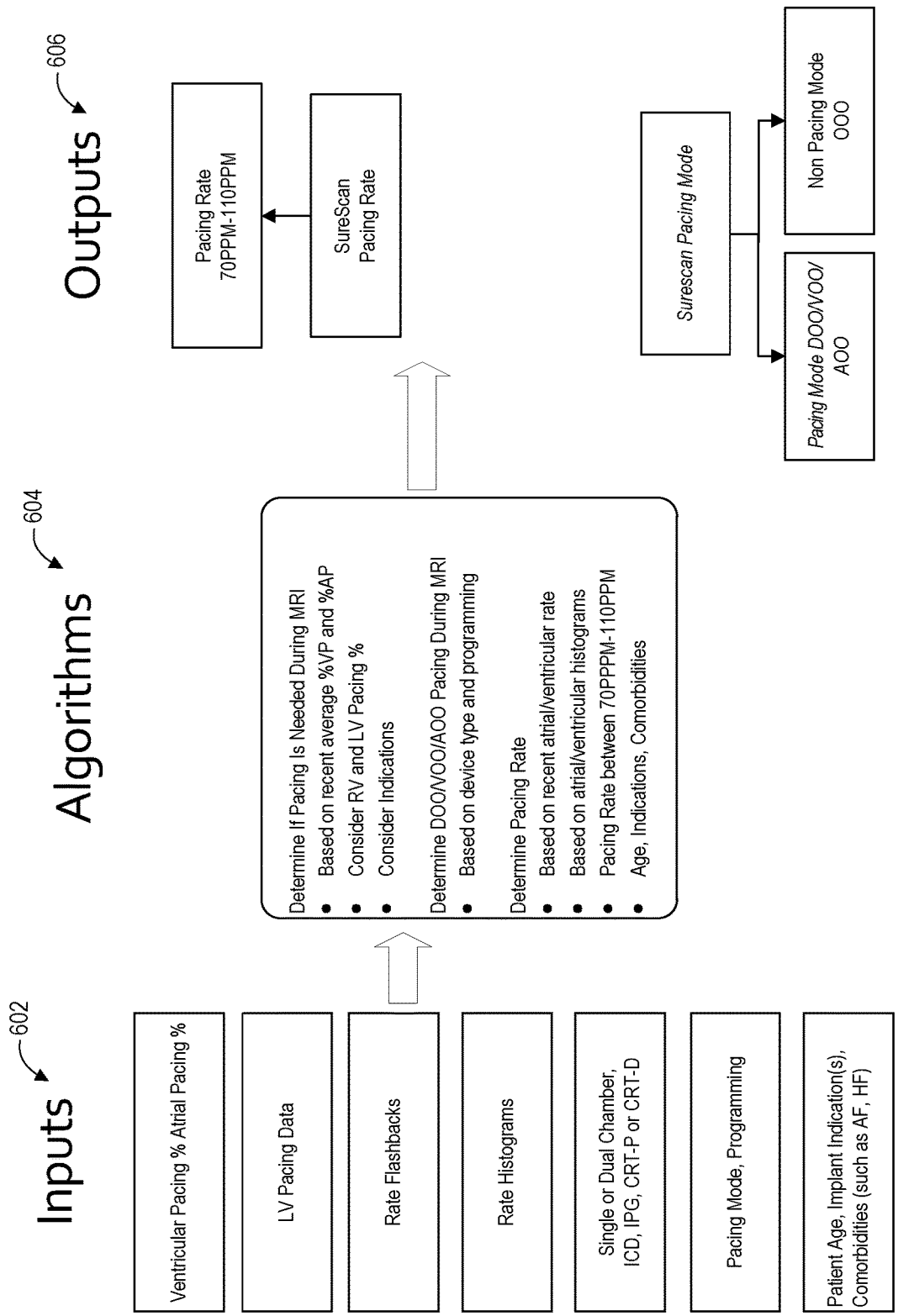
FIG. 6 shows another example of inputs, considerations, and resulting output decisions when implementing an exposure mode of operation at the implantable medical system.

FIG. 6 shows another example of a basic flow of information that may be used by a controller, such as the external device 114 or the internal controller 204, to make a determination as to the appropriate exposure mode and rate of therapy that should be employed. This basic flow of information may also be used to invoke the appropriate exposure mode once it has been detected, either by manual programming or by automatic detection, that the IMD 102 should switch to the exposure mode. The controller may gather information to be used as inputs 602. Examples of the inputs include various pieces of information from the pre-exposure mode operation in addition to those shown in FIG. 3, such as: rate flashbacks and rate histograms, designations of whether the device is a single chamber or dual/triple chamber device, as well as patient specific information including age, implant indications, and comorbidities.

The controller may then process this input information 602 via considerations 604. As discussed for FIG. 3, the controller may determine whether pacing is even needed during the period of time that exposure mode is active, such as during an MRI scan. Factors include what the recent average pacing percentage, right ventricle versus left ventricle pacing percentage, and implant indications.

The considerations 604 may also include determining what the pacing mode should be if pacing is needed, such as whether to pace the atrium, ventricle, or both. This may again be based on the pre-exposure programming as well as current status such as whether atrial fibrillation is occurring and whether a mode switch due to atrial fibrillation is warranted to avoid wasting atrial pacing signals.

The considerations 604 may also include determining the pacing rate. For using asynchronous mode of pacing, the fixed rate may be based on a pre-exposure mode factor such as the recent average atrial or ventricular rate. Furthermore, consideration may be given to a pre-defined range of rates as well as patient age, implant indications, and comorbidities. As with FIG. 3, it may be desirable to contain the fixed rate to a range but in this example, the range is specified as being between 70 and 110 paces per minute. Like that discussed above in FIG. 5A and as further discussed below in reference to FIGS. 9A-9C, in some embodiments it may be desirable to also consider whether it is possible to sense an intrinsic rate that is physiologic rather than artificial while in the exposure mode and in that case trigger pacing from the intrinsic rate rather than using asynchronous pacing at the fixed rate. The result of these considerations 604 is to produce outputs 606 necessary to implement the particular exposure pacing mode rate.

Figure 7:
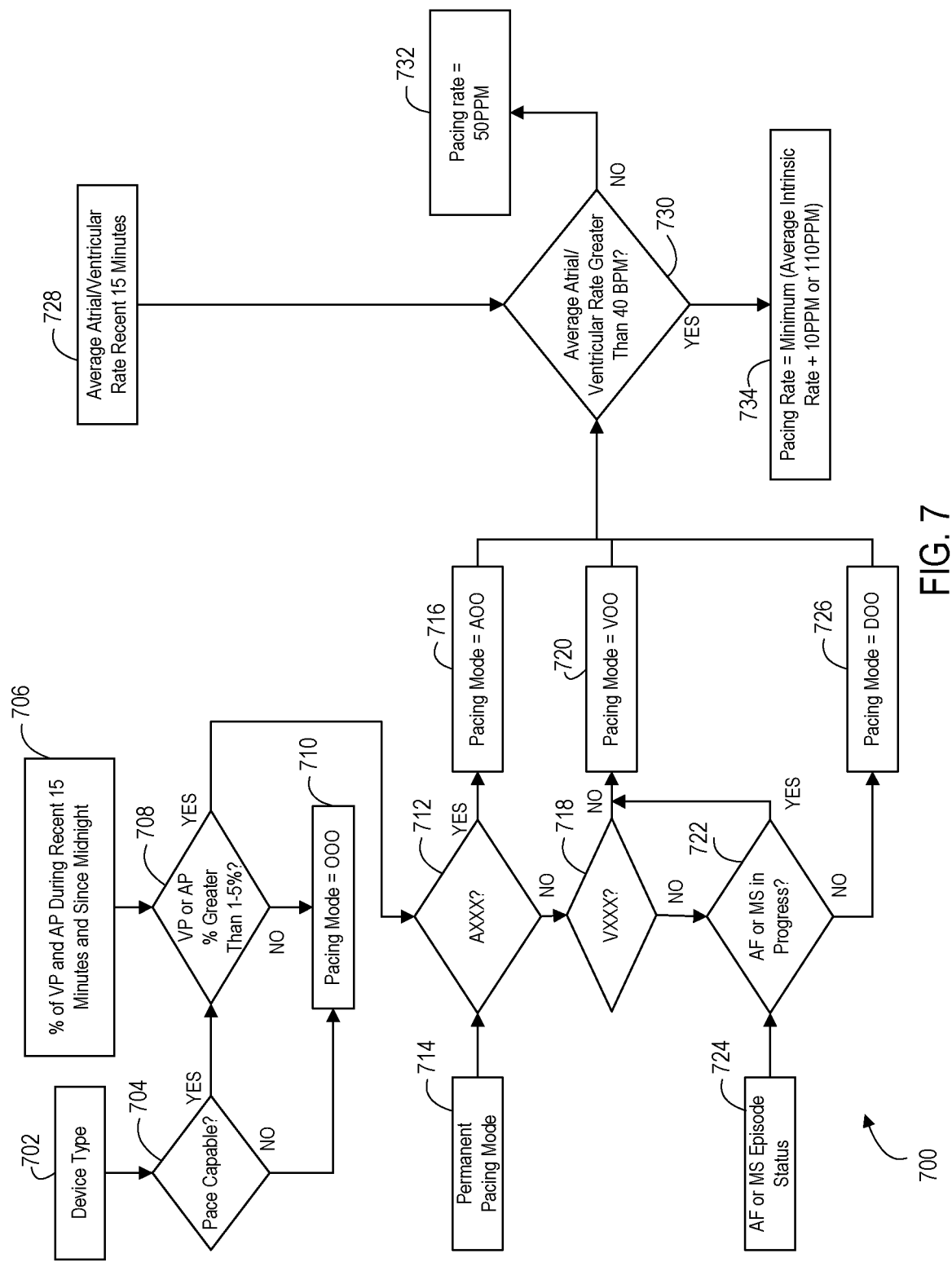
FIG. 7 shows another example of logical operations that may be performed by the implantable medical system to consider device type based on whether the device is pace capable and whether there is an atrial fibrillation in progress and also considers prior rates of cardiac activity when establishing the exposure mode of therapy.

FIG. 7 shows an example 700 of logical operations that may be used to determine the exposure pacing mode to be implanted based on device type, where the device type considerations are whether the device is capable of pacing. The example 700 may further be used to determine whether there is some episode occurring at the time of entering the exposure mode that requires pacing of a given type or lack thereof. Initially, the type of IMD 102 is determined at a query 704 that accesses the device type information 702. For instance, where the controller performing these operations is the external device 114 being used to manually program the IMD 102 to enter the exposure mode, the external device 114 may send a wireless request for information at the query 704 to obtain the device type 702 from the IMD 102. Where the controller 202 of the IMD 102 is the controller performing these operations either in response to a command from the external device 114 to enter the exposure mode or where the IMD 102 has detected the magnetic disturbance and has automatically entered the exposure mode, then the controller 202 accesses the locally stored device type information 702.

Regardless of which device performs these operations, query operation 704 determines from the device type information 702 whether the IMD 102, and specifically the therapy device 208, is of the type that can provide pacing either as the sole mode of therapy or as a mode that is in addition to other modes such as defibrillation or cardiac resynchronization. Operational flow then proceeds to a query operation 708 when the IMD 102 does have pacing ability or otherwise proceeds to set the exposure mode as a non-pacing mode as shown at the pacing mode state 710. While pacing mode state 710 shows the pacing mode as OOO, it will be appreciated that this is just one example of the OXO modes that may be used.

As with the example in FIG. 4, is also to be appreciated that an external device 114 may implement the query 704 and then provide the IMD 102 with instruction regarding whether the controller 204 should then proceed with the remainder of these operations by beginning at the query operation 708 or at setting the non-pacing mode at as shown at state 710. The controller 204 may then proceed with the remainder of these operations where the controller 204 then utilizes pre-exposure mode information without being required to uplink that information to the external device 114. However, where the external device 114 performs all of these operations or where the query 704 is based to some degree on pre-exposure mode programming, then the pre-exposure mode information is uplinked from the IMD 102 to the external device 114 and the external device 114 downlinks the instruction for the proper exposure mode and rate.

It is also to be noted that as in the example of FIG. 4, at query operation 704, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 7 that stems from the query operation 704. In that case, the initial programming being loaded onto the IMD 102 from the manufacturer utilizes the device type information 702 to specify in the initial programming which operation or state should be the first operation to be performed by the IMD 102 upon automatically entering exposure mode, either query operation 708 or non-pacing mode 710. In that case, the IMD 102 need not perform the query operation 704 upon entering the exposure mode since that query 704 was already resolved at the time of initial programming.

In any of these alternatives above, operational flow proceeds to query 708 where the device type is such that pacing is available and proceeds to the state 710 otherwise. For device types leading to the query operation 708, the controller determines from pacing percentage information 706 stored by the IMD 102 whether the pacing percentage (considering atrial and/or ventricular) is greater than a threshold. The pacing percentage information 706 may be based on pacing activity for some pre-exposure period immediately preceding the exposure mode, such as 15 minutes or for the entire day such as since midnight. For example, query 708 may determine whether the IMD 102 has been pacing the atrium or ventricle more than 5% of the pacing cycles for the 15 minutes preceding the exposure mode. It will be appreciated that other pacing percentage thresholds may be also be applied but 5% is believed to be effective for most patients. If the pacing percentage is lower than the threshold, this indicates that it is appropriate for the patient to go without pacing for a short time such as for the duration of an MM scan, and in that case the controller selects that there be no pacing via pacing mode OXO for the exposure mode as indicated at pacing state 710.

If the pacing percentage at the query operation 708 is greater than the pacing threshold, then the controller determines at the sequence of query operations 712 and 718 what the pre-exposure pacing mode has been by referencing the pre-exposure mode pacing mode information 714. This pre-exposure pacing mode, also referred to as the permanent pacing mode, is AXX/AXXR, VXX/VXXR, or DXX/DXXR. The controller sets the exposure mode to pace the same set of chambers as the pre-exposure mode, so where the pre-exposure pacing mode is AXX/AXXR, then in this embodiment the controller selects that there be atrial pacing for the exposure mode by using asynchronous pacing mode AOO as indicated at pacing state 716. Where the pre-exposure pacing mode is VXX/VXXR, then in this embodiment the controller selects that there be ventricular pacing for the exposure mode by using asynchronous pacing mode VOO as indicated at pacing state 720. Where the pre-exposure pacing mode is DXX/DXXR, then in this embodiment the controller performs an additional query operation 722 to determine if there is an atrial fibrillation or mode switch related to an episode of atrial fibrillation that is in progress at the present time based on mode information 724. If so, then even if the permanent mode is dual pacing mode, the controller may select VOO mode at the pacing state 720 to avoid pacing the atrium and conserve energy as the atrial fibrillation may otherwise render the atrial pacing energy superfluous. When there is no atrial fibrillation or mode switch in progress, the controller selects that there be dual chamber pacing for the exposure mode by using asynchronous pacing mode DOO as indicated at pacing state 726.

Once the pacing mode for the exposure mode has been set, the controller then proceeds to a query operation 730 to determine an appropriate exposure mode rate for the chosen pacing mode. The query operation 730 determines whether a pre-exposure mode rate of cardiac activity as specified in pre-exposure mode information 728 exceeds a rate threshold. The pre-exposure mode information 728 may be one of various different pieces of information. For example, the pre-exposure mode information 728 may specify an average ventricular rate taken over a 15 minute period immediately preceding the exposure mode. This pre-exposure mode average rate may be an average intrinsic rate that has been sensed or it may be an average paced rate.

It will be appreciated that the rate threshold applied at the query operation 730 may vary but it has been found that a fixed rate even as low as 40 beats per minute is an effective example. If the threshold is not exceeded by the pre-exposure mode rate, then the controller sets the asynchronous pacing rate to a pre-defined fixed value such as 50 beats per minute as indicated at the pacing rate state 732. It will be appreciated that this pre-defined fixed value may vary, but 50 beats per minute are also known to be acceptable for many patients. If the threshold is exceeded by the pre-exposure mode rate, then the controller sets the asynchronous pacing rate to a fixed value that is equal to the pre-exposure mode rate plus a fixed adjustment but with an upper limit at the pacing rate state 734. For example, the controller may set that asynchronous pacing rate to the pre-exposure rate plus 10 additional paces per minute with an upper limit of 110 paces per minute. The fixed adjustment may vary but it has been found that an adjustment as low as 10 additional paces per minute adequately avoids a competitive pacing condition. Furthermore, the upper limit may vary but it has been found that an upper limit of 110 paces per minute is adequate. Therefore, in this particular example, the pacing rate for the exposure mode will be set within the range of 50-110 paces per minute.

Figure 8:
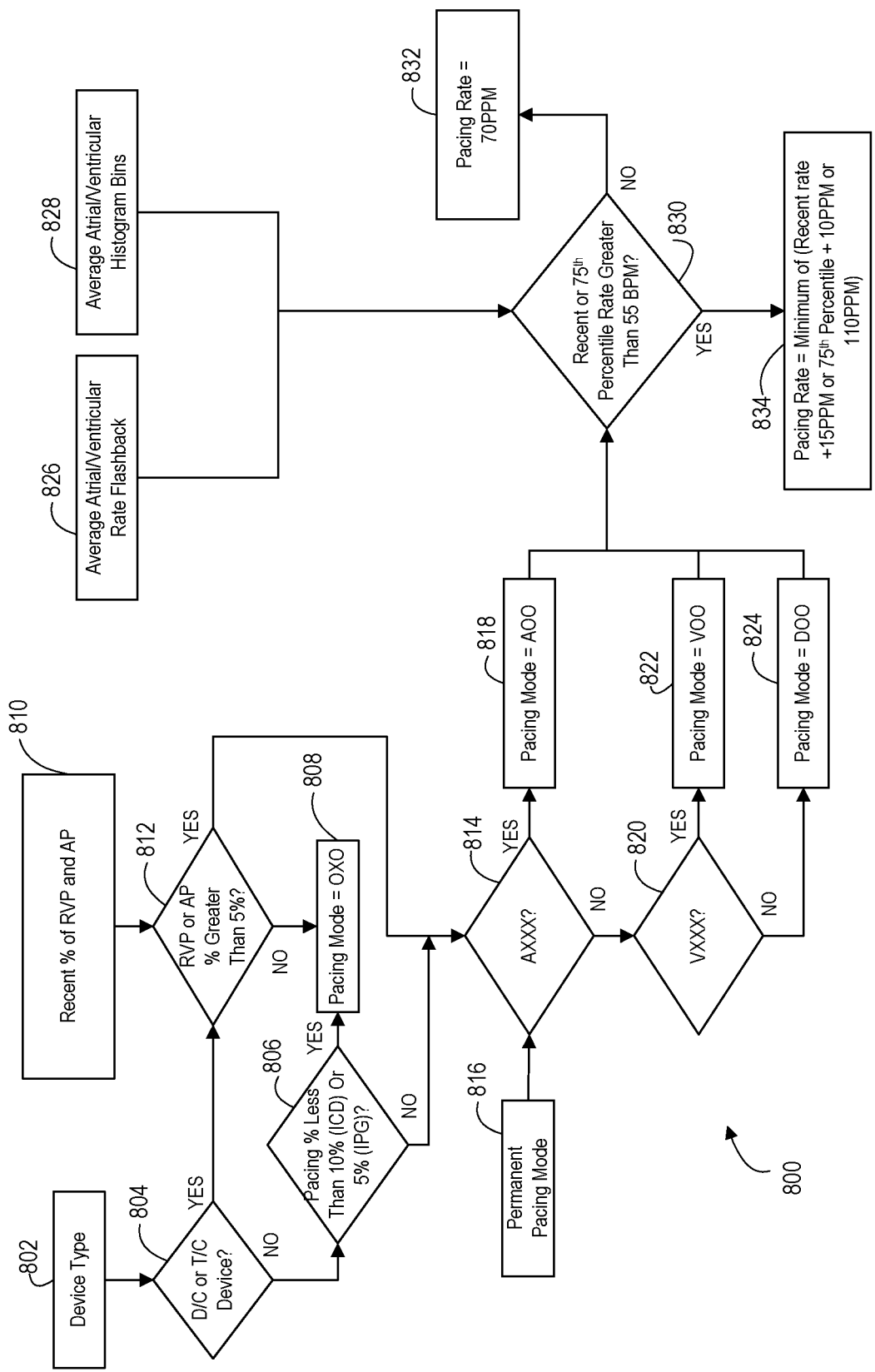
FIG. 8 shows another example of logical operations that may be performed by the implantable medical system to consider device type based on a number of chambers being paced and considers prior rates of cardiac activity when establishing the exposure mode of therapy.

FIG. 8 shows another example 800 of logical operations that may be used to determine the exposure pacing mode to be implanted based on device type, where the device type considerations are whether the device is capable of multi-chamber pacing (i.e., Dual Chamber (D/C) or Triple Chamber (T/C)). Initially, the type of IMD 102 is determined at a query 804 that accesses the device type information 802. Similar to the prior examples, where the controller performing these operations is the external device 114 being used to manually program the IMD 102 to enter the exposure mode, the external device 114 may send a wireless request for information at the query 804 to obtain the device type 802 from the IMD 102. Where the controller 202 of the IMD 102 is the controller performing these operations either in response to a command from the external device 114 to enter the exposure mode or where the IMD 102 has detected the magnetic disturbance and has automatically entered the exposure mode, then the controller 202 accesses the locally stored device type information 802.

Regardless of which device performs these operations, query operation 804 determines from the device type information 802 whether the IMD 102, and specifically the therapy device 208, is of the type that can provide multi-chamber pacing. Operational flow then proceeds to a query operation 812 when the IMD 102 does have multi-chamber pacing ability or otherwise proceeds to a query operation 806 when the device is only single chamber pacing capable.

As with the prior examples, is also to be appreciated that an external device 114 may implement the query 804 and then provide the IMD 102 with instruction regarding whether the controller 204 should then proceed with the remainder of these operations by beginning at the query operation 812 or the query operation 806. The controller 204 may then proceed with the remainder of these operations where the controller 204 then utilizes pre-exposure mode information without being required to uplink that information to the external device 114. However, where the external device 114 performs all of these operations or where the query 804 is based to some degree on pre-exposure mode programming, then the pre-exposure mode information is uplinked from the IMD 102 to the external device 114 and the external device 114 downlinks the instruction for the proper exposure mode and rate.

It is also to be noted that as in the prior examples, at query operation 804, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 8 that stems from the query operation 804. In that case, the initial programming being loaded onto the IMD 102 from the manufacturer utilizes the device type information 802 to specify in the initial programming which operation or state should be the first operation to be performed by the IMD 102 upon automatically entering exposure mode, either query operation 812 or query operation 806. In that case, the IMD 102 need not perform the query operation 804 upon entering the exposure mode since that query 804 was already resolved at the time of initial programming.

In any of these alternatives above, operational flow proceeds to query 812 where the device type is such that multi-chamber pacing is available and proceeds to the query operation 806 otherwise. For device types leading to the query operation 808, the controller determines from pacing percentage information 810 stored by the IMD 102 whether the pacing percentage of either of the multi-chambers (considering atrial and/or right ventricular pacing in this particular example of a multi-chamber device) is greater than a threshold. The pacing percentage information 810 may be based on pacing activity for some pre-exposure period immediately preceding the exposure mode, such as 15 minutes or for the entire day such as since midnight. For example, query 812 may determine whether the IMD 102 has been pacing the atrium or right ventricle more than 5% of the pacing cycles for the 15 minutes preceding the exposure mode. It will be appreciated that other pacing percentage thresholds may be also be applied but 5% is believed to be effective for most patients. If the pacing percentage for both chambers is lower than the threshold, this indicates that it is appropriate for the patient to go without pacing for a short time such as for the duration of an MRI scan, and in that case the controller selects that there be no pacing via pacing mode OXO for the exposure mode as indicated at pacing state 808.

For device types leading instead to the query operation 806, the controller determines from pacing percentage information stored by the IMD 102 for the single chamber pacing whether the pacing percentage of the single chamber is less than a threshold (i.e., does not meet or exceed the threshold). As in the prior examples, the pacing percentage information may be based on pacing activity for some pre-exposure period immediately preceding the exposure mode, such as 15 minutes or for the entire day such as since midnight. The device type may again be used in query operation 806, where one threshold may be applied for devices with defibrillation capability (e.g., 10%) while another threshold is applied for devices with only pacing capability (e.g., 5%) considering that devices with defibrillation capability and low pacing percentage are even more likely to indicate a patient that is tolerant of a non-pacing mode for a relatively short duration such as the length of an MRI scan. It will be appreciated that other pacing percentage thresholds may be also be applied but 10% and 5% are believed to be effective thresholds for most patients. If the pacing percentage is lower than the relevant threshold, this indicates that it is appropriate for the patient to go without pacing during exposure mode, and in that case the controller selects that there be no pacing via pacing mode OXO for the exposure mode as indicated at pacing state 808.

If the pacing percentage for the multi-chamber device at the query operation 812 is greater than the pacing threshold or if the pacing percentage for the single chamber device at the query operation 806 is not less than the device specific single chamber pacing threshold, then the controller determines the exposure mode via the sequence of query operations 814 and 820. The controller considers what the pre-exposure pacing mode has been by referencing the pre-exposure mode pacing mode information 816. This pre-exposure pacing mode, also referred to as the permanent pacing mode, is AXX, VXX, or DXX. The controller sets the exposure mode to pace the same set of chambers as the pre-exposure mode, so where the pre-exposure pacing mode is AXX, then in this embodiment the controller selects that there be atrial pacing for the exposure mode by using asynchronous pacing mode AOO as indicated at pacing state 818. Where the pre-exposure pacing mode is VXX, then in this embodiment the controller selects that there be ventricular pacing for the exposure mode by using asynchronous pacing mode VOO as indicated at pacing state 822. Where the pre-exposure pacing mode is DXX, then in this embodiment the controller selects that there be dual chamber pacing for the exposure mode by using asynchronous pacing mode DOO as indicated at pacing state 824.

Once the pacing mode for the exposure mode has been set, the controller then proceeds to a query operation 830 to determine an appropriate exposure mode rate for the chosen pacing mode. The query operation 830 determines whether a pre-exposure mode rate of cardiac activity as specified in either pre-exposure mode information 826 or alternate pre-exposure mode information 828 exceeds a rate threshold. The pre-exposure mode information 826 may be one of various different pieces of information. For example, the pre-exposure mode information 828 may specify an average atrial and/or ventricular rate taken over a 15 minute period immediately preceding the exposure mode. This pre-exposure mode average rate may be an average intrinsic rate that has been sensed or it may be an average paced rate. The alternate pre-exposure mode information 828 may be a statistical distribution, such as a histogram, based set of information for atrial and/or ventricular cardiac activity, also either paced or intrinsic. This histogram or other statistical distribution information 828 may cover cardiac activity over the entire life of the device or over a particular period of time. A particular percentile from the histogram or other statistical distribution may be chosen as the representative value of pre-exposure mode rate. While the percentile may vary from one embodiment to the next, it has been found that the 75$^{th}$ percentile is an effective value.

It will be appreciated that the rate threshold applied at the query operation 830 may vary but it has been found that a moderate fixed rate like 55 beats per minute is an effective example. If the threshold is not exceeded by the pre-exposure mode rate, then the controller sets the asynchronous pacing rate to a pre-defined fixed value such as 70 paces per minute as indicated at the pacing rate state 832. It will be appreciated that this pre-defined fixed value may vary, but 70 paces per minute are also known to be acceptable for many patients. If the threshold is exceeded by the pre-exposure mode rate, then the controller sets the asynchronous pacing rate to a fixed value that is equal to the pre-exposure mode rate plus a fixed adjustment but with an upper limit at the pacing rate state 834. For example, the controller may set that asynchronous pacing rate to the pre-exposure average rate plus 15 additional paces per minute or the 75$^{th}$ percentile rate plus 10 additional paces per minute, with an upper limit of 110 paces per minute in either case. The fixed adjustment may vary but it has been found that an adjustment as low as 10 additional paces per minute over the 75$^{th}$ percentile or 15 paces per minute over the recent average adequately avoids a competitive pacing condition. Furthermore, the upper limit may vary but it has been found that an upper limit of 110 paces per minute is adequate. Therefore, in this particular example, the pacing rate for the exposure mode will be set within the range of 70-110 paces per minute.

Figure 9A:
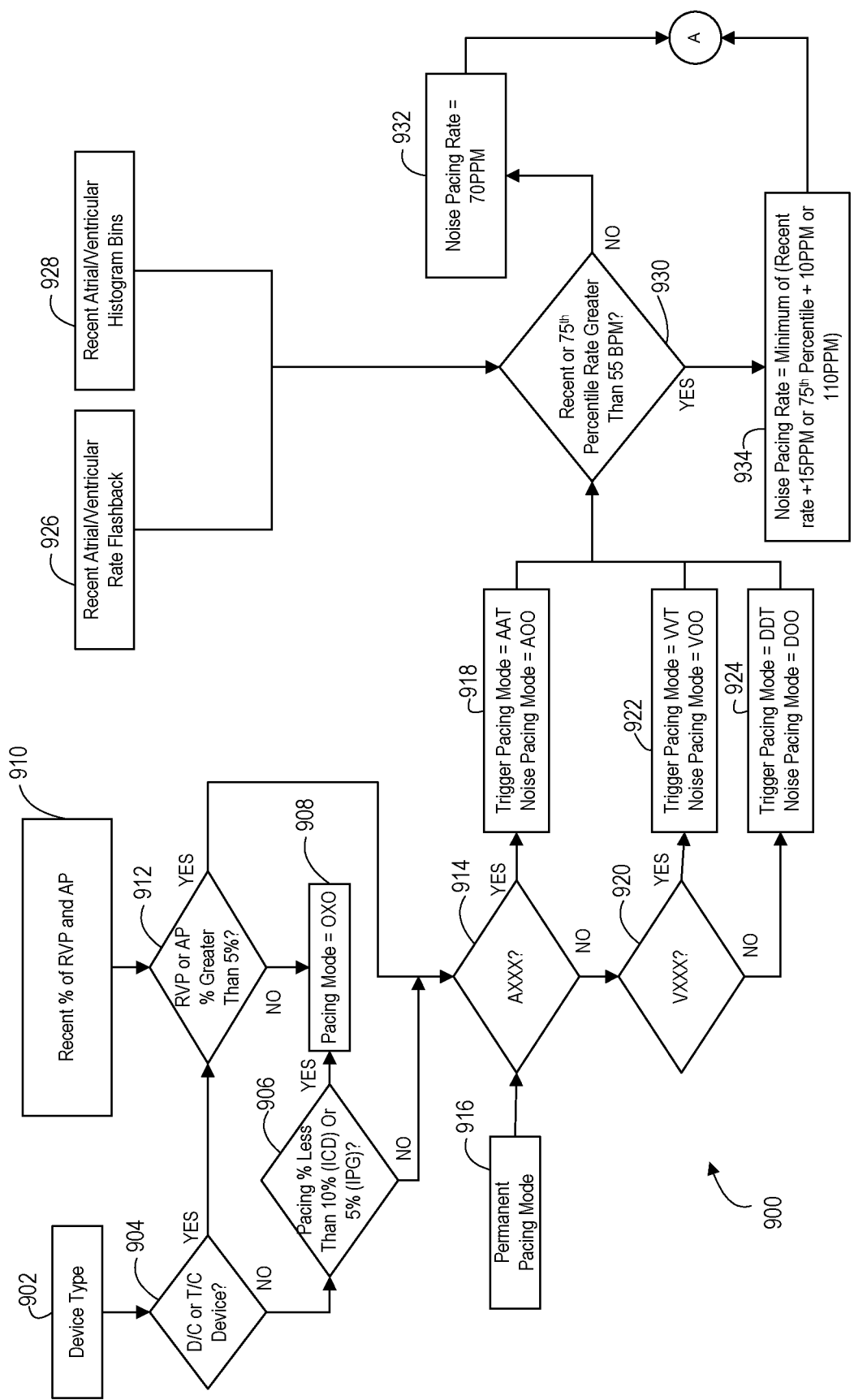
FIG. 9A shows a first portion of another example of logical operations that may be performed by the implantable medical system to consider device type and consider prior rates of cardiac activity when establishing an asynchronous rate in preparation for considering an intrinsic rate to trigger pacing when establishing the exposure mode of therapy.

FIG. 9A shows another example 900 of logical operations that may be used to determine the exposure pacing mode to be implanted based on device type. The example 900 is essentially the same as the example 800 shown in FIG. 8 except that when setting a pacing mode where appropriate, there is both a triggered mode and an asynchronous mode (also referred to as a noise pacing mode) that is selected by the controller. Initially, the type of IMD 102 is determined at a query 904 that accesses the device type information 902. Query operation 904 determines from the device type information 902 whether the IMD 102, and specifically the therapy device 208, is of the type that can provide multi-chamber pacing. Operational flow then proceeds to a query operation 912 when the IMD 102 does have multi-chamber pacing ability or otherwise proceeds to a query operation 906 when the device is only single chamber pacing capable.

As with the prior examples, is also to be appreciated that an external device 114 may implement the query 904 and then provide the IMD 102 with instruction regarding whether the controller 204 should then proceed with the remainder of these operations by beginning at the query operation 912 or the query operation 906. The controller 204 may then proceed with the remainder of these operations where the controller 204 then utilizes pre-exposure mode information without being required to uplink that information to the external device 114. However, where the external device 114 performs all of these operations or where the query 904 is based to some degree on pre-exposure mode programming, then the pre-exposure mode information is uplinked from the IMD 102 to the external device 114 and the external device 114 downlinks the instruction for the proper exposure mode and rate.

It is also to be noted that as in the prior examples, at query operation 904, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 9A that stems from the query operation 904. In that case, the initial programming being loaded onto the IMD 102 from the manufacturer utilizes the device type information 902 to specify in the initial programming which operation or state should be the first operation to be performed by the IMD 102 upon automatically entering exposure mode, either query operation 912 or query operation 906. In that case, the IMD 102 need not perform the query operation 904 upon entering the exposure mode since that query 904 was already resolved at the time of initial programming.

In any of these alternatives above, operational flow proceeds to query 912 where the device type is such that multi-chamber pacing is available and proceeds to the query operation 906 otherwise. For device types leading to the query operation 912, the controller determines from pacing percentage information 910 stored by the IMD 102 whether the pacing percentage of either of the multi-chambers (considering atrial and/or right ventricular pacing in this particular example of a multi-chamber device) is greater than a threshold. The pacing percentage information 910 may be based on pacing activity for some pre-exposure period immediately preceding the exposure mode, such as 15 minutes or for the entire day such as since midnight. For example, query 912 may determine whether the IMD 102 has been pacing the atrium or right ventricle more than 5% of the pacing cycles for the 15 minutes preceding the exposure mode. It will be appreciated that other pacing percentage thresholds may be also be applied but 5% is believed to be effective for most patients. If the pacing percentage for both chambers is lower than the threshold, this indicates that it is appropriate for the patient to go without pacing for a short time such as for the duration of an MRI scan, and in that case the controller selects that there be no pacing via pacing mode OXO for the exposure mode as indicated at pacing state 908.

For device types leading instead to the query operation 906, the controller determines from pacing percentage information stored by the IMD 102 for the single chamber pacing whether the pacing percentage of the single chamber is less than a threshold (i.e., does not meet or exceed the threshold). As in the prior examples, the pacing percentage information may be based on pacing activity for some pre-exposure period immediately preceding the exposure mode, such as 15 minutes or for the entire day such as since midnight. The device type may again be used in query operation 906, where one threshold may be applied for devices with defibrillation capability (e.g., 10%) while another threshold is applied for devices with only pacing capability (e.g., 5%) considering that devices with defibrillation capability and low pacing percentage are even more likely to indicate a patient that is tolerant of a non-pacing mode for a relatively short duration such as the length of an MRI scan. It will be appreciated that other pacing percentage thresholds may be also be applied. If the pacing percentage is lower than the relevant threshold, this indicates that it is appropriate for the patient to go without pacing during exposure mode, and in that case the controller selects that there be no pacing via pacing mode OXO for the exposure mode as indicated at pacing state 908.

If the pacing percentage for the multi-chamber device at the query operation 912 is greater than the pacing threshold or if the pacing percentage for the single chamber device at the query operation 906 is not less than the device specific single chamber pacing threshold, then the controller determines the exposure mode via the sequence of query operations 914 and 920. The controller considers what the pre-exposure pacing mode has been by referencing the pre-exposure mode pacing mode information 916. This pre-exposure pacing mode, also referred to as the permanent pacing mode, is AXX/AXXR, VXX/VXXR, or DXX/DXXR. The controller sets the exposure mode to pace the same set of chambers as the pre-exposure mode. In this embodiment, the controller selects an asynchronous or noise pacing mode as well as a triggered pacing mode based on the chamber(s) being paced in the pre-exposure mode. So where the pre-exposure pacing mode is AXX/AXXR, then in this embodiment the controller selects that there be atrial pacing for the exposure mode by selecting an asynchronous pacing mode AOO and a triggered pacing mode AAT as indicated at pacing state 918. Where the pre-exposure pacing mode is VXX/VXXR, then in this embodiment the controller selects that there be ventricular pacing for the exposure mode by selecting an asynchronous pacing mode VOO and a triggered pacing mode VVT as indicated at pacing state 922. Where the pre-exposure pacing mode is DXX/DXXR, then in this embodiment the controller selects that there be dual chamber pacing for the exposure mode by selecting an asynchronous pacing mode DOO and a triggered pacing mode DDT as indicated at pacing state 924.

Once the pacing mode for the exposure mode has been set, the controller then proceeds to a query operation 930 to determine an appropriate asynchronous exposure mode rate for the chosen pacing mode. The query operation 930 determines whether a pre-exposure mode rate of cardiac activity as specified in either pre-exposure mode information 926 or alternate pre-exposure mode information 928 exceeds a rate threshold. The pre-exposure mode information 826 may be one of various different pieces of information. For example, the pre-exposure mode information 828 may specify an average atrial and/or ventricular rate taken over a 15 minute period immediately preceding the exposure mode. This pre-exposure mode average rate may be an average intrinsic rate that has been sensed or it may be an average paced rate. The alternate pre-exposure mode information 828 may be a statistical distribution, such as a histogram, based set of information for atrial and/or ventricular cardiac activity, also either paced or intrinsic. This histogram or other statistical distribution information 828 may cover cardiac activity over the entire life of the device or over a particular period of time. A particular percentile from the histogram, such as the 75$^{th}$ percentile for instance, may be chosen as the representative value of pre-exposure mode rate. As noted in the prior example 800, the percentile may vary from one embodiment to the next, but it has been found that the 75$^{th}$ percentile is an effective value.

It will again be appreciated that the rate threshold applied at the query operation 930 may vary but it has been found that a moderate fixed rate like 55 beats per minute is an effective example. If the threshold is not exceeded by the pre-exposure mode rate, then the controller sets the asynchronous pacing rate to a pre-defined fixed value such as 70 paces per minute as indicated at the pacing rate state 932. It will be appreciated that this pre-defined fixed value may vary, but 70 paces per minute are also known to be acceptable for many patients. If the threshold is exceeded by the pre-exposure mode rate, then the controller sets the asynchronous pacing rate to a fixed value that is equal to the pre-exposure mode rate plus a fixed adjustment but with an upper limit at the pacing rate state 934. As in the example 800 of FIG. 8, the controller may set that asynchronous pacing rate to the pre-exposure average rate plus 15 additional paces per minute or the 75$^{th}$ percentile rate plus 10 additional paces per minute, with an upper limit of 110 paces per minute in either case. The fixed adjustment may vary in either case as previously discussed. Furthermore, the upper limit may vary but as previously stated it has been found that an upper limit of 110 paces per minute is adequate. Therefore, in this particular example, the pacing rate for the exposure mode will be set within the range of 70-110 paces per minute.

Figure 9B:
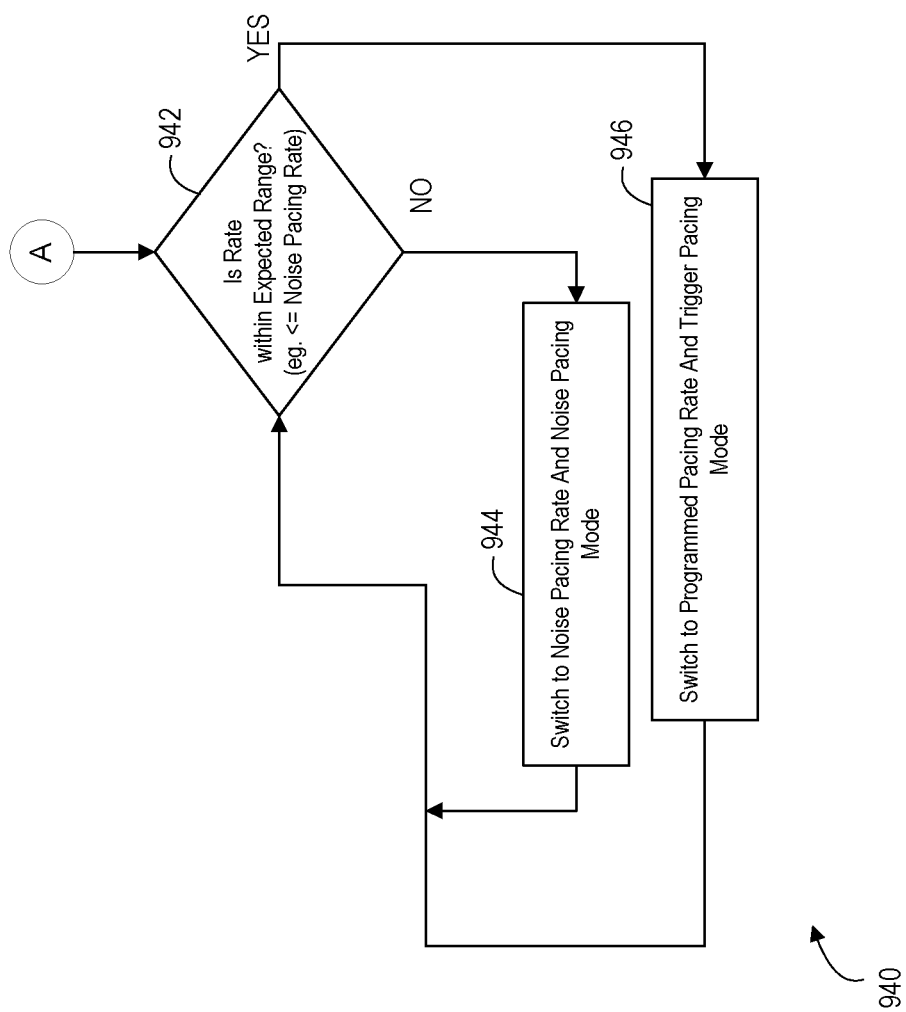
FIG. 9B shows one example of a second portion of the logical operations being continued from FIG. 9A where the intrinsic rate is considered to determine whether to use triggered pacing.

Because the exposure mode of this embodiment has a triggered mode and an asynchronous mode, additional logic is utilized to determine when to use one versus the other based on whether the intrinsic mode is likely to be physiologic or artificial. One example 940 of this additional logic is shown in FIG. 9B. Here at a query operation 942, the controller determines whether the sensed intrinsic rate is within an expected range. As discussed above in relation to the example of FIG. 5A, the expected or normal range of the intrinsic rate may be determined based on a range of percentiles from the pre-exposure histogram or other statistical distribution information, centered on the average pre-exposure rate, or from a pre-defined range. As another example, the expected range may be specified as anything equal to or lesser than the previously established asynchronous or noise pacing rate from FIG. 9A. As yet another example, the expected range may be based on the formula 220-age of the patient to establish an upper limit on the expected range.

If the intrinsic rate is within the expected range, which suggests the intrinsic rate is physiologic rather than artificially produced by a magnetic disturbance, the controller then activates the triggered pacing mode, which has been previously established in FIG. 9A, at a pacing state 946. If the intrinsic rate is outside of the expected range, then the controller activates the asynchronous pacing mode and corresponding asynchronous pacing rate, both of which have also been previously established in FIG. 9A, at a pacing state 944. This process of the controller determining whether the sensed intrinsic rate is in the expected range and implementing either the triggered or asynchronous mode repeats throughout the duration of the exposure mode by continuously sensing the intrinsic rate and continuously determining which mode of pacing to activate.

Figure 9C:
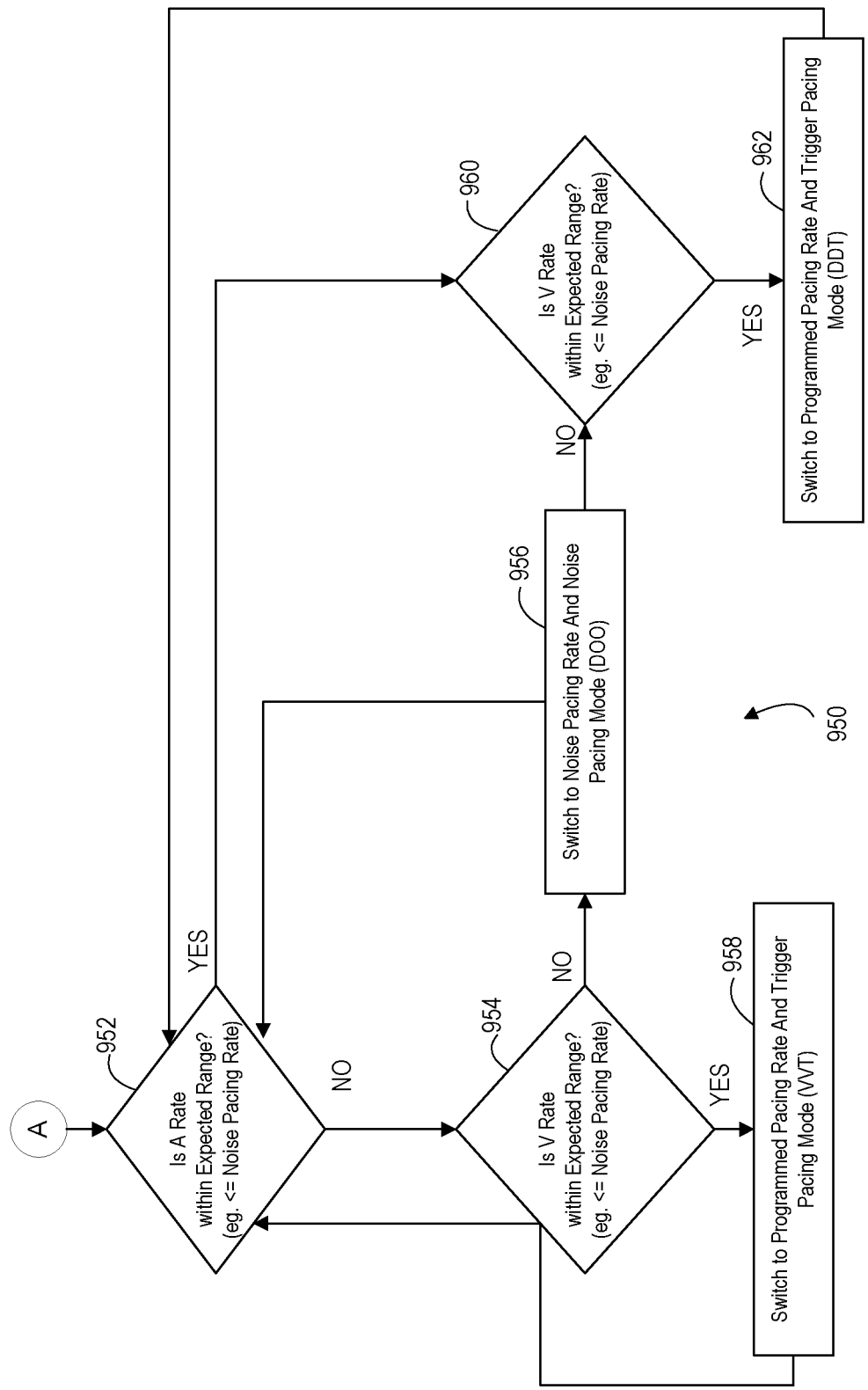
FIG. 9C shows a second example of a second portion of the logical operations being continued from FIG. 9A where both atrial and ventricular rates are considered to determine whether to use atrial and/or ventricular triggered pacing.

Another example 950 of the additional logic that may be used by the controller when choosing between triggered pacing mode and asynchronous pacing mode as the exposure mode of therapy is shown in FIG. 9C. In this example, the pacing mode previously established in FIG. 9A is for dual mode pacing. However, these logical operations account for the possibility that the sensed intrinsic rate of one chamber to be paced may be in the expected range while the sensed intrinsic rate of the other chamber to be paced may not.

In this example, the controller detects whether the sensed intrinsic atrial rate is in the expected range at a query operation 952. Again, the expected or normal range for the atrial rate may be specified in various ways such as in terms of a range of percentiles of the histogram of atrial rate data, a range centered on the pre-exposure atrial rate average, or a pre-defined range. As another example, the expected atrial range may be specified as anything equal to or lesser than the previously established asynchronous or noise pacing rate from FIG. 9A. As yet another example, the expected atrial range may be based on the formula 220-age of the patient to establish an upper limit on the expected range. If the atrial rate is expected, then the controller determines whether the ventricular intrinsic rate is within the expected range at operation 960. The expected or normal range for the ventricular rate may also be specified in various ways such as in terms of a range of percentiles of the histogram of ventricular rate data, a range centered on the pre-exposure ventricular average, or a pre-defined range. As another example, the expected ventricular range may be specified as anything equal to or lesser than the previously established asynchronous or noise pacing rate from FIG. 9A. As yet another example, the expected ventricular range may be based on the formula 220-age of the patient to establish an upper limit on the expected range.

When the ventricular rate is also within the expected range, then the controller determines that the dual chamber triggered pacing mode is appropriate and then selects the dual chamber triggered mode DDT at pacing state 962. When the ventricular rate is not within the expected range, suggesting that it is not physiologic, even though the atrial rate is within the expected range, the dual chamber asynchronous mode is most appropriate. Therefore, the controller then selects the dual chamber asynchronous mode DOO at the pacing mode state 956.

Returning to query operation 952, when the controller determines that the atrial rate is not within the expected range, the controller then determines whether the ventricular rate is within the expected range at a query operation 954. If the ventricular rate is also outside of the expected range, then the dual chamber asynchronous mode is again most appropriate. Therefore, the controller then selects the dual chamber asynchronous mode DOO at the pacing mode state 956. If the ventricular rate is within the expected range, then switching away from dual chamber pacing to allow for triggered ventricular pacing is most appropriate. Therefore, the controller then selects the triggered ventricular mode VVT at the pacing mode state 958. This process of the controller determining whether the sensed intrinsic atrial and ventricular rates are in the expected range and implementing the triggered or asynchronous dual chamber mode or the triggered ventricular mode repeats throughout the duration of the exposure mode by continuously sensing the intrinsic atrial and ventricular rates and continuously determining which mode of pacing to activate.

Figure 9D:
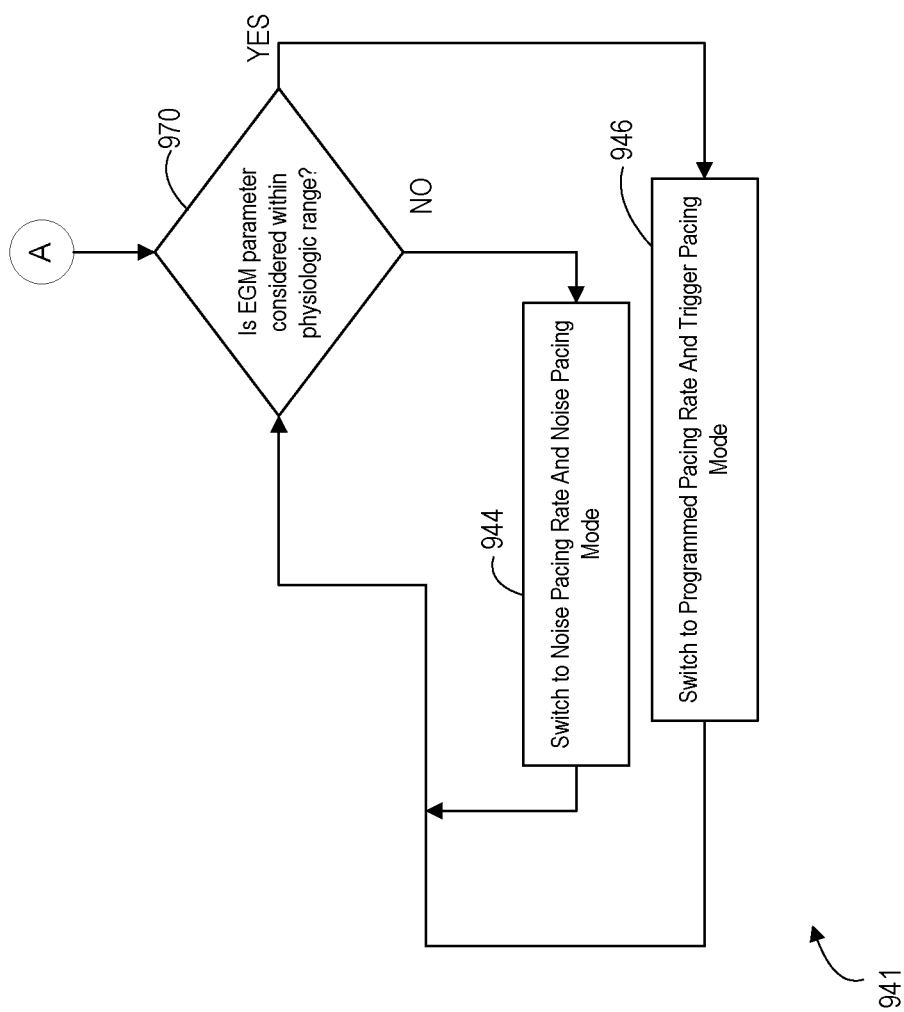
FIG. 9D shows a third example of a second portion of the logical operations being continued from FIG. 9A where an electrogram parameter is considered to determine whether to use triggered pacing.

FIG. 9D shows another example 941 of logical operations, similar to that of FIG. 9B, except that in FIG. 9D electrogram (EGM) parameters captured by the device 102 are analyzed at a query operation 970 to determine whether the EGM parameters are physiologic. One example of the EGM parameters includes the morphology of the cardiac signal, which can be compared to a template to determine whether the morphology matches the template within a certain degree of accuracy. Another example of the EGM parameters includes the frequency content of the cardiac signal, where frequency content outside of a physiologic frequency band is indicative of an artificial source. If the EGM parameters are physiologic, then a sensed rate is considered to be a reliable physiologic rate that can be used for triggered pacing mode at the pacing state 946. If the EGM parameters are not considered to be in a physiologic range, then a sensed rate is considered to be an unreliable artificial rate that should not be used for triggered pacing mode and so asynchronous pacing is chosen at the pacing state 944.

Figure 9E:
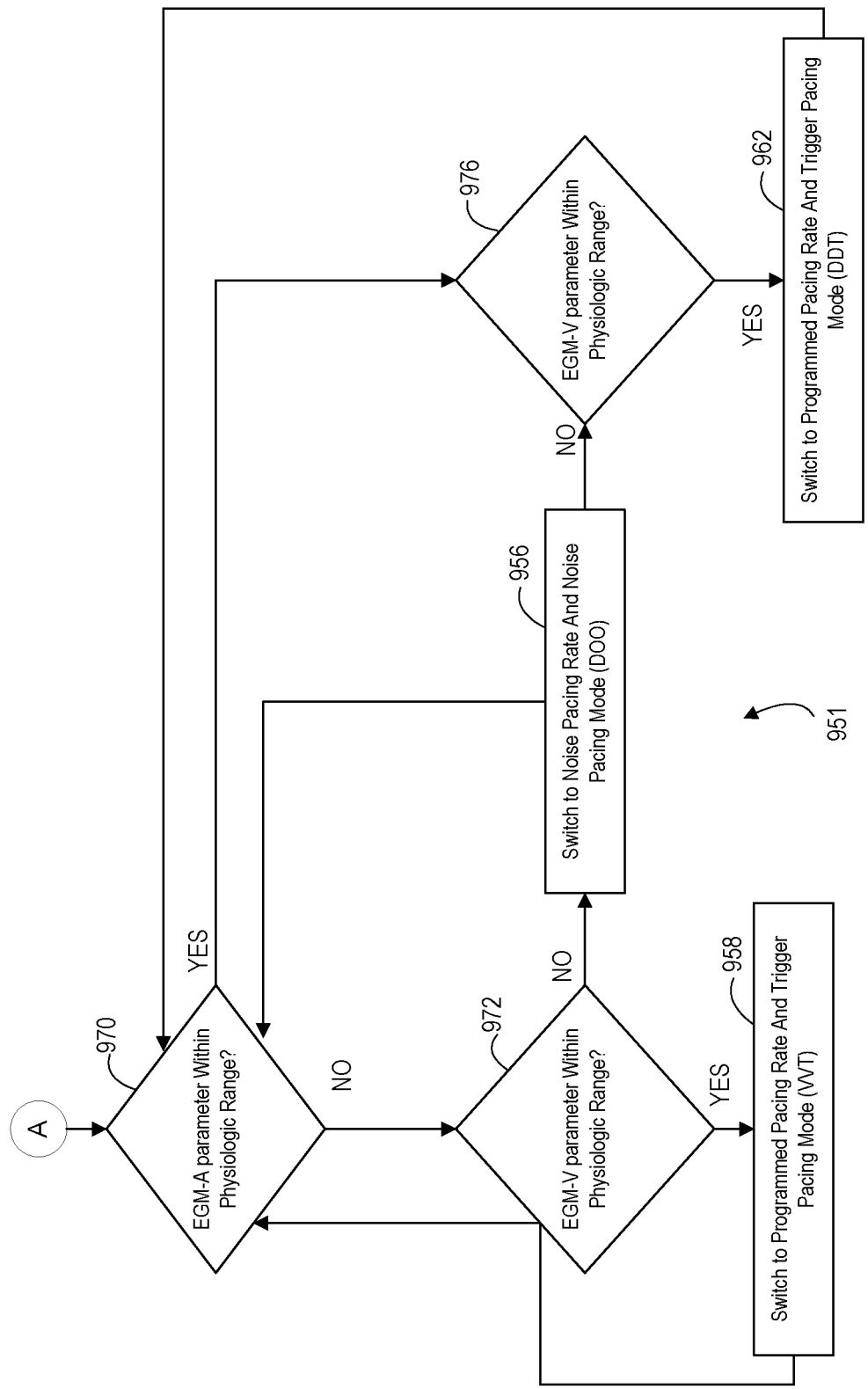
FIG. 9E shows a fourth example of a second portion of the logical operations being continued from FIG. 9A where both atrial and ventricular electrogram parameters are considered to determine whether to use atrial and/or ventricular triggered pacing.

FIG. 9E shows another example 951 of logical operations, similar to that of FIG. 9C, except that in FIG. 9E EGM parameters captured by the device 102 are analyzed to determine if the EGM parameters are within the physiologic range. In particular, query 970 detects whether atrial EGM parameters are within the physiologic range. If query 970 detects that the atrial EGM parameters are physiologic, then operational flow proceeds to query operation 976 where it is determined whether the ventricular EGM parameters are within the physiologic range. Where the ventricular EGM parameters are physiologic, then DDT mode is chosen at the DDT state 962 and where the ventricular EGM parameters are not physiologic, then DOO mode is chosen at the DOO state 956. If query 970 detects that the atrial EGM parameters are not physiologic, then operational flow proceeds to query operation 972 where it is determined whether the ventricular EGM parameters are within the physiologic range. Where the ventricular EGM parameters are physiologic, then VVT mode is chosen at the VVT state 958 and where the ventricular EGM parameters are not physiologic, then DOO mode is chosen at the DOO state 956. Some examples of the atrial and ventricular EGM parameters may include those discussed above with reference to FIG. 9D, such as cardiac signal morphology and frequency content.

Figure 10:
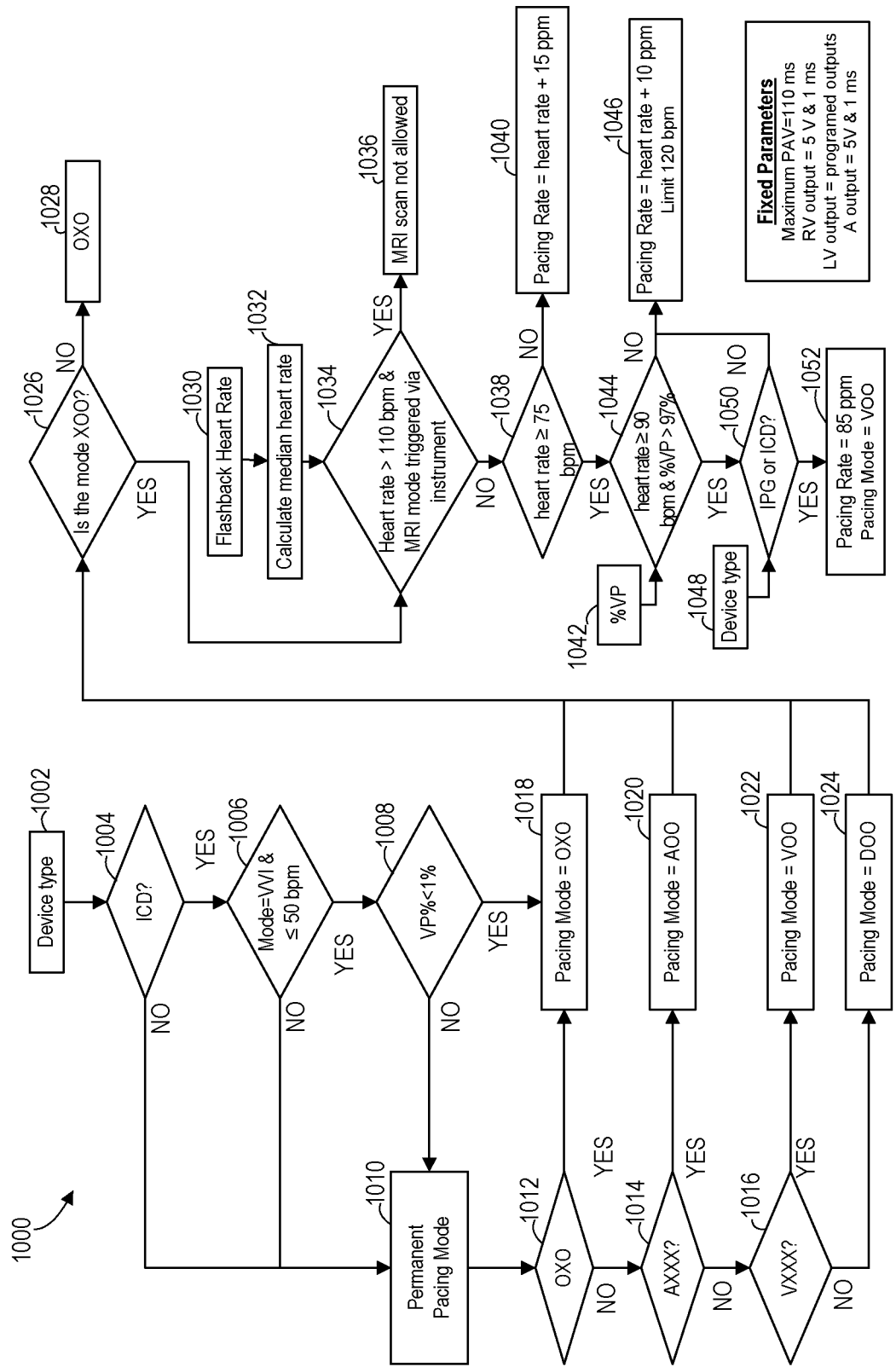
FIG. 10 shows another example of logical operations that may be performed by the implantable medical system to consider device type and prior rates of cardiac activity when establishing the exposure mode of therapy.

FIG. 10 shows another example 1000 of logical operations that a controller may employ to ultimately select the pacing mode and rate for the exposure mode of therapy. Initially, the type of IMD 102 is determined at a query 1004 that accesses the device type information 1002. For instance, where the controller performing these operations is the external device 114 being used to manually program the IMD 102 to enter the exposure mode, the external device 114 may send a wireless request for information at the query 1004 to obtain the device type 1002 from the IMD 102. Where the controller 202 of the IMD 102 is the controller performing these operations either in response to a command from the external device 114 to enter the exposure mode or where the IMD 102 has detected the magnetic disturbance and has automatically entered the exposure mode, then the controller 202 accesses the locally stored device type information 1002.

Regardless of which device performs these operations, query operation 1004 determines from the device type information 1002 whether the IMD 102, and specifically the therapy device 208, is of the type that can provide defibrillation. For instance, query operation 1004 may specifically check for an ICD or a CRT device with defibrillation. Operational flow then proceeds to a query operation 1006 when the IMD 102 does have defibrillation ability or proceeds to query operation 1012 when the IMD 102 does not have defibrillation ability.

It is also to be appreciated that an external device 114 may implement the query 1004 and then provide the IMD 102 with instructions regarding whether the controller 204 should then proceed with the remainder of these operations by beginning at the query operation 1006 or at the query operation 1012. The controller 204 may then proceed with the remainder of these operations where the controller 204 then utilizes pre-exposure mode information without being required to uplink that information to the external device 114. However, where the external device 114 performs all of these operations or where the query 1004 is based to some degree on pre-exposure mode programming (e.g., CRT-D with defibrillation deactivated to behave as a CRT-P), then the pre-exposure mode information is uplinked from the IMD 102 to the external device 114 and the external device 114 downlinks the instruction for the proper exposure mode and rate.

It is also to be noted that at query operation 1004, it is possible in some embodiments that no pre-exposure mode information has been needed because the type of device is entirely hardware based and not affected by pre-exposure programming. In that case an IMD 102 that has the ability to automatically enter the exposure mode may be programmed by the manufacturer regarding which branch of logic to use in FIG. 10 that stems from the query operation 1004. In that case, the initial programming being loaded onto the IMD 102 from the manufacturer utilizes the device type information 1002 to specify in the initial programming which query operation should be the first operation to be performed by the IMD 102 upon automatically entering exposure mode, either query operation 1006 or query operation 1012. In that case, the IMD 102 need not perform the query operation 1004 upon entering the exposure mode since that query 1004 was already resolved at the time of initial programming.

In any of these alternatives above, operational flow proceeds to query 1006 where the device type is such that defibrillation is available and proceeds to the query operation 1012 otherwise. For device types leading to the query operation 1006

For device types and configurations leading to the query operation 1008, the controller determines from the ventricular pacing percentage (VP %) information stored by the IMD 102 whether the ventricular pacing percentage is less than a relatively low threshold, such as less than 1%. The ventricular pacing percentage information may be based on pacing activity for some pre-exposure period immediately preceding the exposure mode, such as 15 minutes or for the entire day such as since midnight. For example, query 1006 may determine whether the IMD 102 has been pacing the ventricle less than 1% of the pacing cycles for the 15 minutes preceding the exposure mode. As has been previously discussed herein, it will be appreciated that various pacing percentage thresholds may also be applied but 1% is believed to be an effective amount for most patients when applying this example of logical operations. If the pacing percentage is lower than the threshold, this indicates that it is appropriate for the patient to go without pacing for a short time such as for the duration of an MRI scan, and in that case the controller selects that there be no pacing via pacing mode OXO for the exposure mode as indicated at pacing state 1018. If the pacing percentage at the query operation 1008 is greater than the pacing threshold, then the operational flow proceeds directly to the query operation 1012.

At the sequence of query operations 1012, 1014, and 1016, the controller then determines what the pre-exposure pacing mode has been by referencing the pre-exposure mode pacing mode information 1010. As previously discussed, this pre-exposure pacing mode, also referred to as the permanent pacing mode, is AXX/AXXR, VXX/VXXR, or DXX/DXXR but may also be a mode where pacing is not being provided but sensing may be occurring. Query 1012 determines if the permanent pacing mode is such that no pacing is occurring and in that case sets the pacing mode to OXO at the operation 1018. The controller sets the exposure mode to pace the same set of chambers as the pre-exposure mode, so where the pre-exposure pacing mode is AXX/AXXR, then in this embodiment the controller selects that there be atrial pacing for the exposure mode by using asynchronous pacing mode AOO as indicated at pacing state 1020. Where the pre-exposure pacing mode is VXX/VXXR, then in this embodiment the controller selects that there be ventricular pacing for the exposure mode by using asynchronous pacing mode VOO as indicated at pacing state 1022. Where the pre-exposure pacing mode is DXX/DXXR, then in this embodiment the controller selects that there be dual chamber pacing for the exposure mode by using asynchronous pacing mode DOO as indicated at pacing state 1024.

Once the pacing mode for the exposure mode has been set, the controller then proceeds to a query operation 1026 to begin the determination of an appropriate exposure mode pacing rate for the chosen pacing mode. The query operation 1026 determines if the pacing mode is set to a non-pacing mode. If so, then the non-pacing mode with no pacing rate is maintained at the pacing mode state 1028. If a mode that does pace has been set then a subsequent query operation is performed depending upon the circumstances of entering the MRI mode. If the implantable medical device is being programmed into the MRI mode by the external instrument, then query operation 1034 may be performed, either by the implantable device upon being triggered by the external instrument or by the external instrument itself. At query operation 1034, it is determined whether a pre-exposure mode rate of cardiac activity as specified in pre-exposure mode information established by rate information 1030 and calculation operation 1032 exceeds a rate threshold.

The pre-exposure mode information may be one of various different pieces of information. For example, the pre-exposure mode information may specify a median ventricular rate taken over a 15 minute period immediately preceding the exposure mode that is calculated by the calculation operation 1032 from the rate information 1030. This pre-exposure mode rate may be a median intrinsic rate that has been sensed or it may be a median paced rate. It will be appreciated that other mathematical calculations besides a median calculation may be utilized, such as calculating the mean intrinsic rate or the mean paced rate.

At the query operation 1034, where the MIll mode is being triggered by the external device, it is determined whether the calculated heart rate exceeds a first threshold that is relatively high, such as 110 beats per minute. If so, then the Mill scan should not be performed without getting an additional review and programming from the responsible cardiac clinician. Where the query operation 1034 is being performed by the external instrument, that instrument then signals to the clinician that the MM scan should not be allowed without a review at an operation 1036. Where the query operation 1034 is being performed by the implantable medical device, the implantable medical device communicates with the external instrument to signal that the MM should not be performed without a review, and then the external instrument signals the same to the clinician at the operation 1036.

Where the calculated heart rate is found to be below the first threshold at the query operation 1034, a query operation 1038 then determines whether the heart rate exceeds a second threshold that is moderate, such as 75 beats per minute. If the calculated rate is under the second threshold, then the pacing rate is set to the calculated heart rate plus a moderate upward adjustment amount, such as 15 beats per minute, to establish a moderate fixed rate. Where the calculated heart rate is found to be above the second threshold, then operational flow proceeds to a query operation 1044.

At the query operation 1044, it is determined whether the calculated heart rate exceeds a third threshold and whether the VP %, provided as information 1042 which matches the information used at the query operation 1008 discussed above, exceeds a relatively high VP % threshold, such as 97%. The third threshold is between the moderate second threshold and the relative high first threshold, such as 90 beats per minute. If the calculated heart rate does not exceed the third threshold and/or the VP % does not exceed the VP % threshold, then the pacing rate is set to the calculated heart rate plus an upward adjustment, typically smaller than the adjustment at operation 1040, such as 10 beats per minute at an operation 1046. Also, at operation 1046, the rate is capped at with an upper limit, such as 120 beats per minute.

If both the third threshold is exceeded by the calculated heart rate and the VP % exceeds the VP % threshold, then operation flow proceeds to a query 1050. Here, it is determined whether the device type as specified in information 1048, which is the same as information 1002 discussed above, is an implantable pulse generator or an implantable defibrillator. If not, meaning the device is likely a cardiac resynchronization therapy device with or without defibrillation, then operational flow proceeds back to operation 1046 where the rate as discussed above for operation 1046 is applied. If the device is an implantable pulse generator or an implantable defibrillator, then operational flow proceeds to operation 1052. Here, the pacing rate is set to a moderate level such as 85 beats per minute. Note that when operational flow reaches operation 1052, the pacing mode is VOO.

Additional information related to the pacing mode includes parameters that may remain fixed. A maximum pacing atrial to ventricular pacing (PAV) limit may be set to a fixed value such as 110 ms to minimize the risk of pacing on a T-wave. If the permanent PAV is already less than this value, then PAV interval may not be extended. Right Ventricular (RV) pacing amplitude and width and Right Atrial (RA) pacing amplitude and width may be set to a fixed value to assure a safety pacing margin and pacing support during an MIll scan. LV amplitude may be maintained at an existing programmed setting for amplitude and width because setting a higher amplitude may result in phrenic stimulations that hinder MIll imaging.

While embodiments have been particularly shown and described, it will be understood by those skilled in the art that various other changes in the form and details may be made therein without departing from the spirit and scope of the invention.

What is claimed is:

1. A method for controlling an exposure mode of therapy of an implantable medical device comprising:
   determining whether a sensed heart rate of a patient exceeds a first threshold;
   when the sensed heart rate does not exceed the first threshold, then selecting a pacing rate for the exposure mode that is equal to the sensed heart rate plus a first adjustment;
   when the sensed heart rate does exceed the first threshold, determining that the sensed heart rate does not exceed a second threshold that is higher than the first threshold and/or a ventricular pacing percentage does not exceed a pacing percentage threshold;
   when the sensed heart rate does not exceed the second threshold and/or the ventricular pacing percentage does not exceed the pacing percentage threshold, then selecting the pacing rate for the exposure mode that is equal to the sensed heart rate plus a second adjustment; and
   at least one of causing an external device to provide an instruction about the exposure mode to the implantable medical device and/or causing the implantable medical device to enter the exposure mode.

2. The method of claim 1, further comprising when the sensed heart rate does exceed the second threshold and the ventricular pacing percentage does exceed the pacing percentage threshold, then selecting a pacing rate for the exposure mode based on a device type of the implantable medical device.

3. The method of claim 2, further comprising:
   determining the device type is other than a cardiac resynchronization therapy device; and setting the pacing rate to a fixed amount higher than the first threshold and lower than the second threshold when the device type is other than a cardiac resynchronization therapy device.

4. The method of claim 3, further comprising setting a pacing mode to a VOO mode when the device type is other than a cardiac resynchronization therapy device.

5. The method of claim 2, further comprising:
   determining the device type is other than a cardiac resynchronization therapy device; and setting the pacing rate to be equal to the heart rate plus the second adjustment when the device type is a cardiac resynchronization therapy device.

6. The method of claim 1, wherein selecting the pacing rate for the exposure mode when the sensed heart rate does not exceed the second threshold and/or the ventricular pacing percentage does not exceed the pacing percentage threshold comprises selecting the pacing rate for the exposure mode that is equal to the sensed heart rate plus a second adjustment but limited to a specified maximum pacing rate.

7. The method of claim 1, further comprising:
   determining a device type of the implantable medical device; and
   selecting a pacing mode for the exposure mode based at least on the device type.

8. The method of claim 1, further comprising:
   determining one or more of a device type of the implantable medical device, a pre-exposure pacing mode of the implantable medical device and/or the ventricular pacing percentage; and
   selecting a pacing mode for the exposure mode based at least on the one or more of the device type of the implantable medical device, the pre-exposure pacing mode of the implantable medical device, and/or the ventricular pacing percentage.

9. The method of claim 8, wherein the pacing mode for the exposure mode comprises one of an OXO, AOO, VOO and DOO pacing mode.

10. A device for controlling an exposure mode of therapy of an implantable medical device comprising:
a controller configured to:
determine whether a sensed heart rate of a patient exceeds a first threshold;
when the sensed heart rate does not exceed the first threshold, select a pacing rate for the exposure mode that is equal to the sensed heart rate plus a first adjustment;
when the sensed heart rate does exceed the first threshold, determine that the sensed heart rate does not exceed a second threshold that is higher than the first threshold and/or a ventricular pacing percentage does not exceed a pacing percentage threshold;
when the sensed heart rate does not exceed the second threshold and/or the ventricular pacing percentage does not exceed the pacing percentage threshold, then select the pacing rate for the exposure mode that is equal to the sensed heart rate plus a second adjustment; and
at least one of cause the device to provide an instruction about the exposure mode to the implantable medical device and/or cause the implantable medical device to enter the exposure mode.

11. The device of claim 10, wherein the controller is further configured to determine the sensed heart rate does exceed the second threshold and the ventricular pacing percentage does exceed the pacing percentage threshold and select a pacing rate for the exposure mode based on a device type of the implantable medical device in response to determining the sensed heart rate does exceed the second threshold and the ventricular pacing percentage does exceed the pacing percentage threshold.

12. The device of claim 11, wherein the controller is further configured to:
determine the device type is other than a cardiac resynchronization therapy device; and set the pacing rate to a fixed amount higher than the first threshold and lower than the second threshold when the device type is other than a cardiac resynchronization therapy device.

13. The device of claim 12, wherein the controller is further configured to set a pacing mode to a VOO mode when the device type is other than a cardiac resynchronization therapy device.

14. The device of claim 11, wherein the controller is further configured to:
determine the device type is other than a cardiac resynchronization therapy device; and set the pacing rate to be equal to the heart rate plus the second adjustment when the device type is a cardiac resynchronization therapy device.

15. The device of claim 10, wherein the controller is further configured to select the pacing rate for the exposure mode that is equal to the sensed heart rate plus a second adjustment but limited to a specified maximum pacing rate when the sensed heart rate does not exceed the second threshold and/or the ventricular pacing percentage does not exceed the pacing percentage threshold.

16. The device of claim 10, wherein the controller is further configured to: determine a device type of the implantable medical device; and
select a pacing mode for the exposure mode based at least on the device type.

17. The device of claim 10, wherein the controller is further configured to:
determine one or more of a device type of the implantable medical device, a pre-exposure pacing mode of the implantable medical device and/or the ventricular pacing percentage; and
select a pacing mode for the exposure mode based at least on the one or more of the device type of the implantable medical device, the pre-exposure pacing mode of the implantable medical device, and/or the ventricular pacing percentage.

18. The device of claim 17, wherein the pacing mode for the exposure mode comprises one of an OXO, AOO, VOO and DOO pacing mode.

19. The device of claim 10, wherein the device comprises an external device, the external device further comprising:
a telemetry component configured to communicate via wireless communication, wherein the controller is further configured to obtain information, including at least the sensed heart rate, from the implantable medical device via wireless communication and provide an instruction about the exposure mode of therapy to the implantable medical device via the wireless communication.

20. The device of claim 10, wherein the device comprises the implantable medical device, the implantable medical device further comprising:
a telemetry component configured to communicate via wireless communication,
wherein the controller is further configured to select the pacing rate in response to one of a command received via wireless communication to enter the exposure mode or in response to a detected the magnetic disturbance.

* * * * *